United States Patent
Saab

(10) Patent No.: US 9,486,632 B2
(45) Date of Patent: *Nov. 8, 2016

(54) PAIN MANAGEMENT

(71) Applicant: Rhode Island Hospital, Providence, RI (US)

(72) Inventor: Carl Y. Saab, Providence, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/632,420

(22) Filed: Feb. 26, 2015

(65) Prior Publication Data

US 2015/0231395 A1 Aug. 20, 2015

Related U.S. Application Data

(63) Continuation of application No. 13/643,670, filed as application No. PCT/US2011/034203 on Apr. 27, 2011, now Pat. No. 8,977,362.

(60) Provisional application No. 61/328,583, filed on Apr. 27, 2010.

(51) Int. Cl.
 *A61N 1/36* (2006.01)
(52) U.S. Cl.
 CPC ....... *A61N 1/36071* (2013.01); *A61N 1/36125* (2013.01); *A61N 1/36139* (2013.01)
(58) Field of Classification Search
 CPC ................. A61N 1/36021; A61N 1/36071; A61N 1/36125; A61N 1/36139; A61N 1/361
 USPC .......................................................... 607/46
 See application file for complete search history.

(56) References Cited

U.S. PATENT DOCUMENTS

| | | | |
|---|---|---|---|
| 7,894,905 B2* | 2/2011 | Pless | A61N 1/36071 607/46 |
| 2003/0100931 A1* | 5/2003 | Mullett | A61N 1/36071 607/46 |
| 2005/0010262 A1* | 1/2005 | Rezai | A61N 1/36071 607/46 |
| 2007/0265683 A1* | 11/2007 | Ehrlich | A61N 1/0534 607/55 |

OTHER PUBLICATIONS

Changes in electrophysiological properties and sodium channel Nav1.3 expression in thalamic neurons after spinal cord injury; Bryan C. Hains, Carl. Y. Saab and Stephen G. Waxman, Brain (2005), 128, 2359-2371.*
High-Frequency Stimulation Produces a Transient Blockade of Voltage-Gated Currents in Subthalmic Neurons; Corinne Burrier, Bernard Bioulac, Jacques Audin, and Constance Hammond; J Neurophysiology 85:1351-1356, 2001.*

* cited by examiner

*Primary Examiner* — Paula J Stice
(74) *Attorney, Agent, or Firm* — Mintz Levin Cohn Ferris Glovsky and Popeo, P.C.

(57) ABSTRACT

Data characterizing a signal of electrical activity sensed in a patient can be received using at least one data processor. A pain signature associated with peripheral nerve damage can be detected using the received data. A treatment protocol can be determined in response to the detected pain signature. The treatment protocol can include providing at least one electrical signal to the patient comprising one or more electrical pulses being at least about 150 Hz, between about 1 and about 3 volts, between about 1 and about 3 milliampere, and between about 0.25 and about 1 second in duration. The treatment protocol to be delivered to a sensory thalamus contained within the patient via an electrical lead and electrode implantable within the sensory thalamus. The treatment protocol can be caused to be initiated.

16 Claims, 32 Drawing Sheets

FIG. 12B
Mean spikes/burst | Mean burst interspike (ms) | Mean burst length (ms)
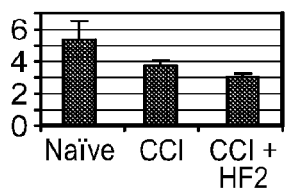 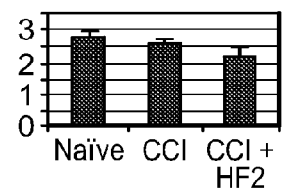 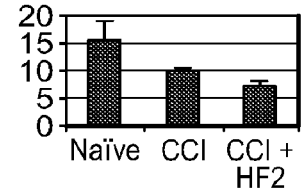
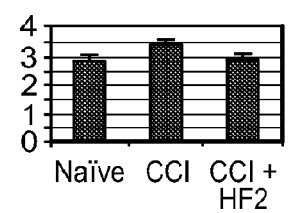 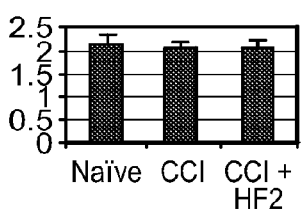 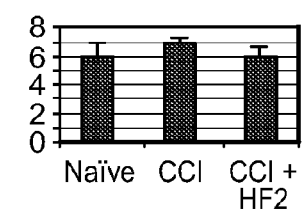
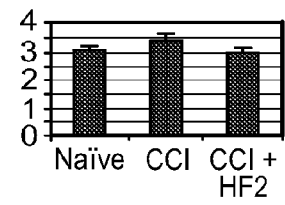 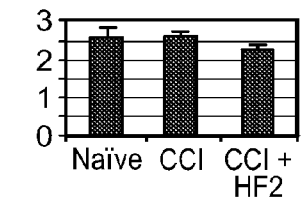 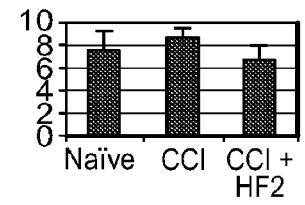
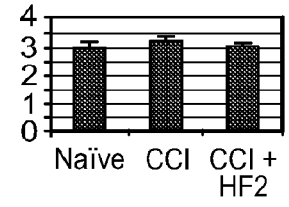 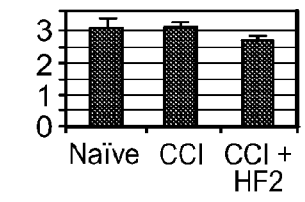 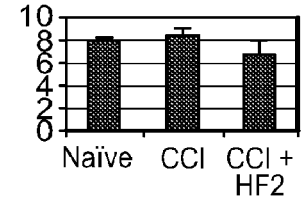
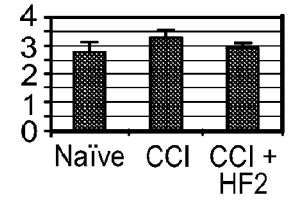 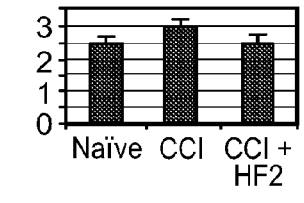 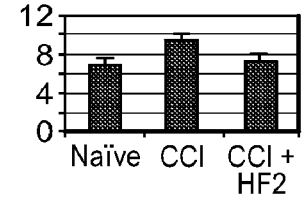
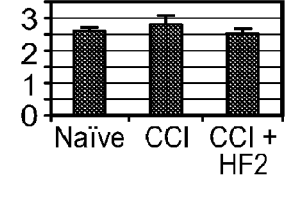 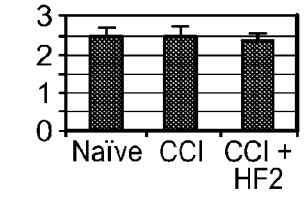 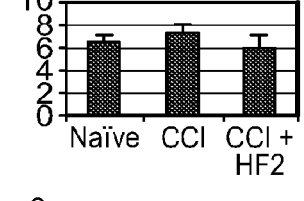
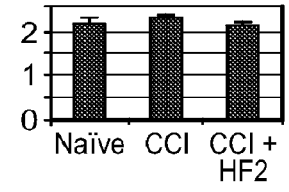 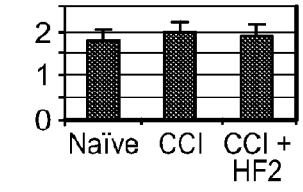 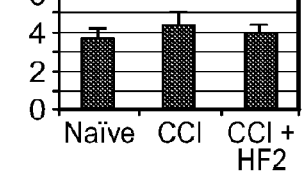

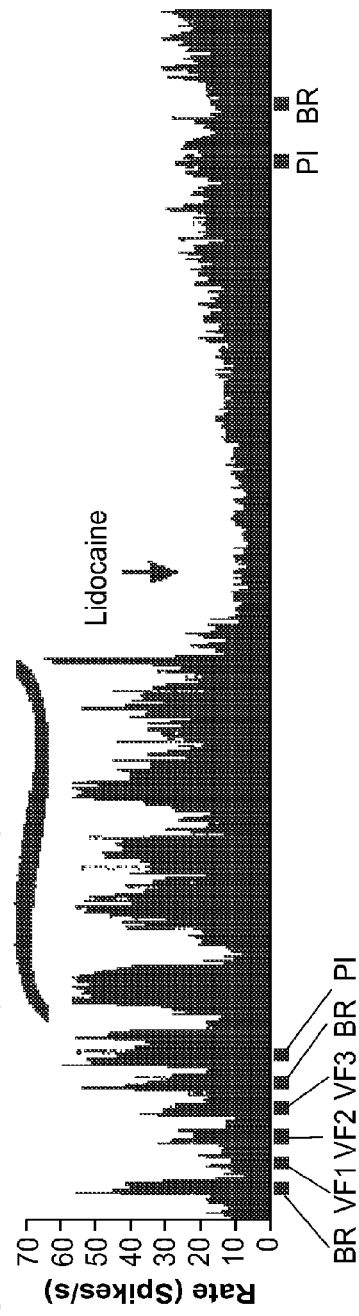
FIG. 13
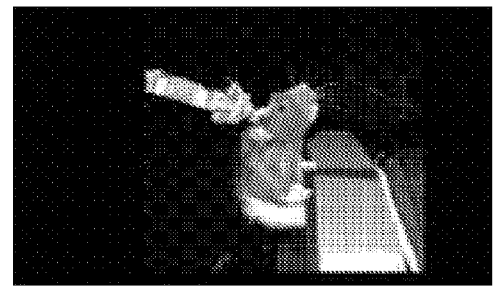
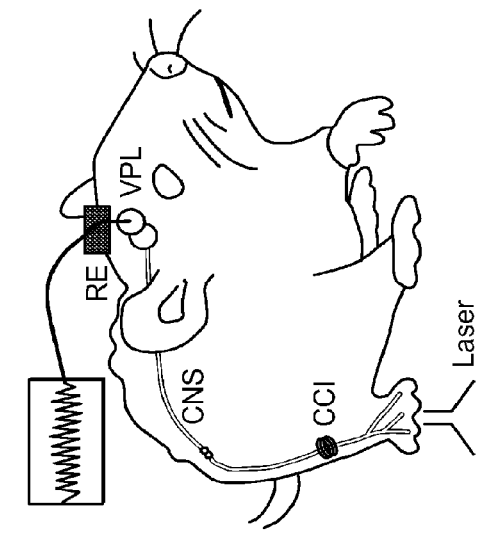
FIG. 14

FIG. 15
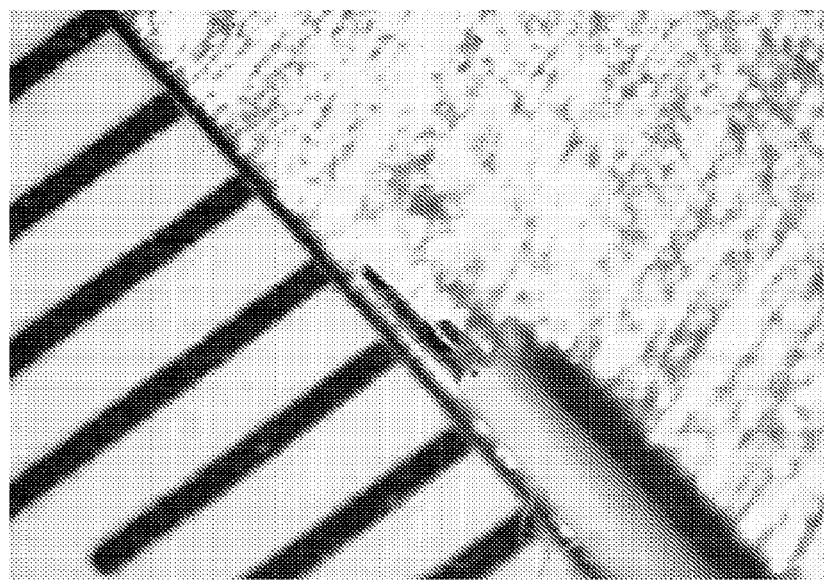
FIG. 16
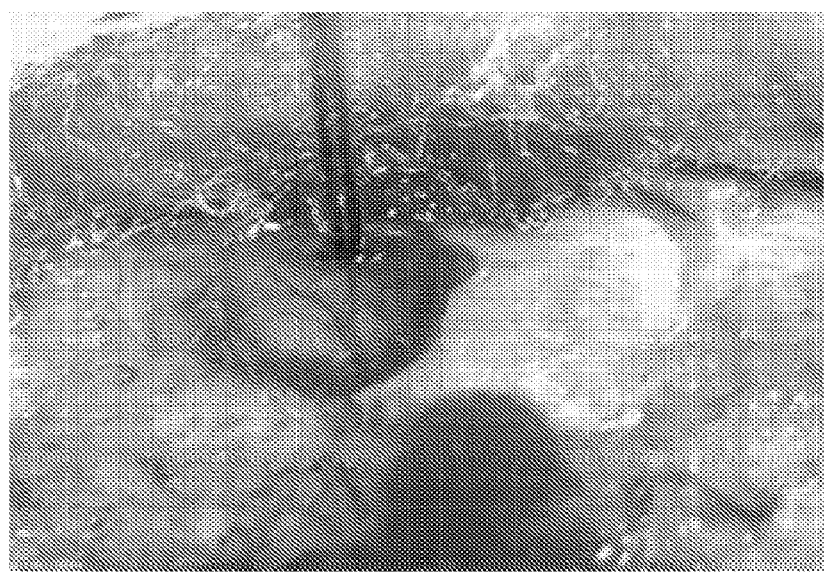
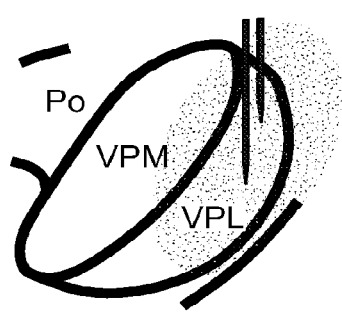
FIG. 17

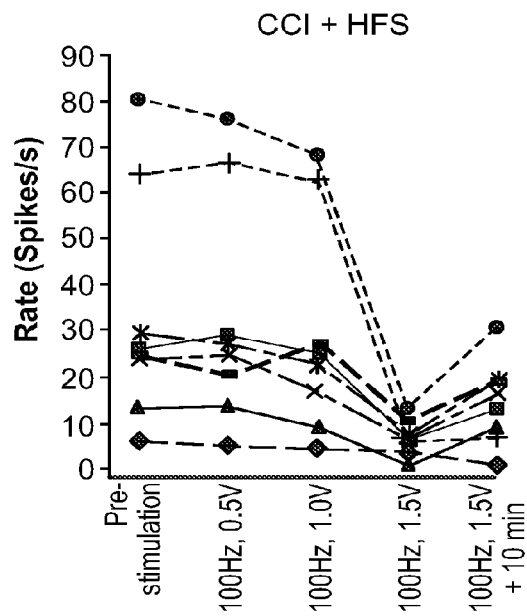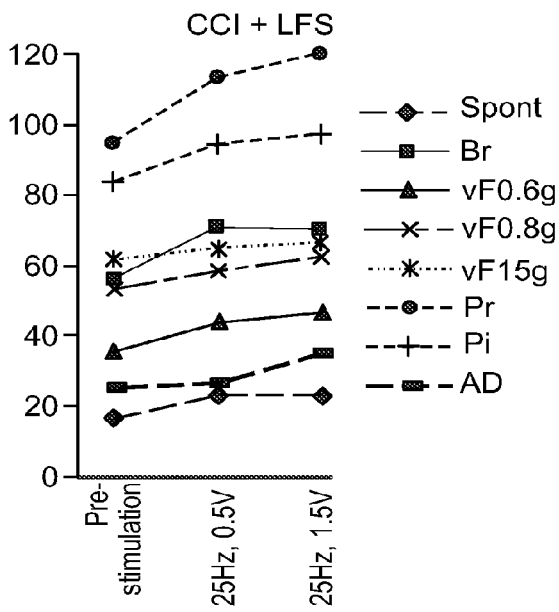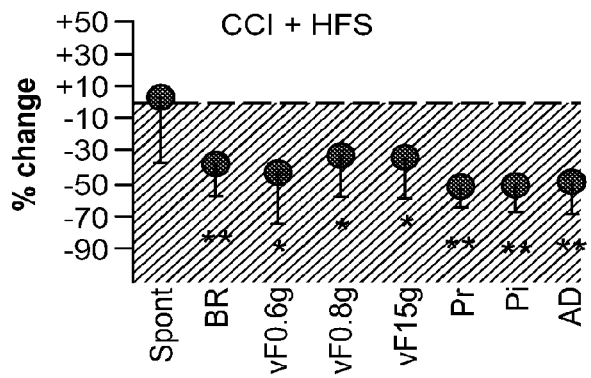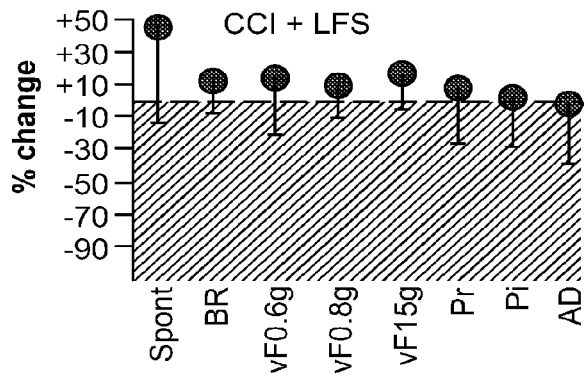

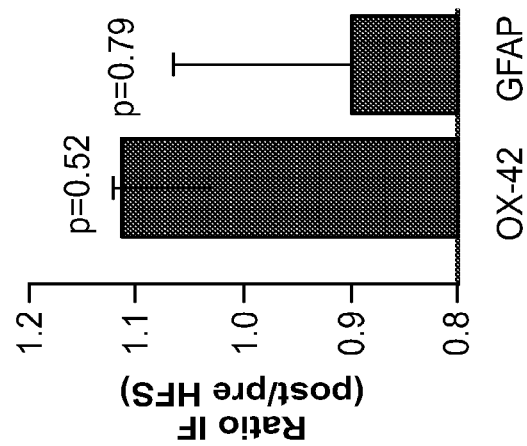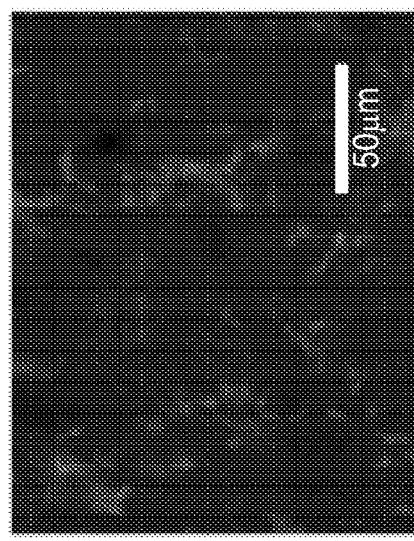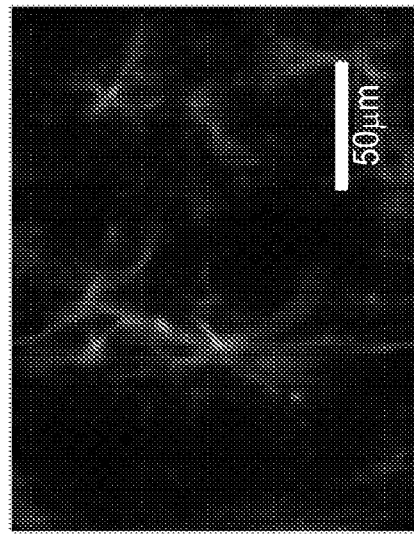
FIG. 28

| Table 1: Rate of firing (spikes/s) | | | | | | | | |
|---|---|---|---|---|---|---|---|---|
| | | Spont | Br | vF0.6 | vF0.8 | vF1.5 | Pr | Pi | AD |
| Naïve | | 0.2 ± 0.1 | 21.2 ± 9.3 | 4.7 ± 1.7 | 14.4 ± 5.8 | 17.0 ± 4.3 | 18.8 ± 4.5 | 26.8 ± 7.9 | 7.6 ± 3.5 |
| CCI | | 6.4 ± 2.4 * | 18.4 ± 3.5 | 3.2 ± 1.1 | 14.2 ± 3.4 | 17.3 ± 4.1 | 65.1 ± 17.4 * | 63.6 ± 14.5 * | 26.1 ± 5.8 * |

| Table 2: Percent rate of firing relative to pre-stimulation (100%) | | | | | | | | |
|---|---|---|---|---|---|---|---|---|
| | Spont | Br | vF0.6 | vF0.8 | vF1.5 | Pr | Pi | AD |
| CCI+HFS | 103.6 ± 40.4 | 62.1 ± 20.9 ** | 57.1 ± 33.0 * | 67.0 ± 25.5 * | 65.9 ± 24.2 * | 47.9 ± 12.4 ** | 48.1 ± 15.9 ** | 50.9 ± 18.2 ** |
| CCI+LFS | 145.7 ± 60.0 | 111.6 ± 19.0 | 113.7 ± 33.8 | 110.8 ± 21.0 | 115.9 ± 20.8 | 108.2 ± 33.5 | 102.0 ± 30.0 | 96.0 ± 33.7 |

FIG. 29B

Table 3: Percent rate of firing relative to pre-stimulation (100%)

|  | Spont | Br | vF0.6 | vF0.8 | vF1.5 | Pr | Pi | AD |
|---|---|---|---|---|---|---|---|---|
| CCI+mHFS | 106.4 ± 58.1 | 87.7 ± 31.3 | 88.7 ± 59.7 | 94.2 ± 42.4 | 91.2 ± 38.6 | 61.2 ± 21.7* | 59.2 ± 26.6* | 53.3 ± 28.7* |
| Naïve+HFS |  | 69.2 ± 12.9* | 79.7 ± 9.9 | 60.5 ± 16.1* | 52.2 ± 14.9* | 49.4 ± 18.3** | 57.1 ± 15.6** | 79.7 ± 46.7 |

Table 4: Burst analysis

|  |  | Spont | Br | vF0.6 | vF0.8 | vF1.5 | Pr | Pi | AD |
|---|---|---|---|---|---|---|---|---|---|
| Burst events | Naïve | 0.4 ± 0.3 | 83.84 ± 15.0 | 20.2 ± 4.8 | 13.0 ± 11.0 | 45.8 ± 11.8 | 50.4 ± 23.1 | 63.7 ± 15.3 | 6.7 ± 3.5 |
|  | CCI | 12.2 ± 5.9* | 115.4 ± 18.5* | 49.8 ± 16.2* | 125.1 ± 34.7* | 141.0 ± 39.5* | 300.1 ± 61.3* | 251.6 ± 62.2* | 43.8 ± 12.6* |
|  | CCI+HFS | 8.0 ± 3.7* | 83.4 ± 30.2* | 34.1 ± 18.4* | 84.1 ± 36.2* | 102.4 ± 47.4 | 141.9 ± 55.6# | 113.7 ± 54.8# | 24.6 ± 10.2 |
| % spikes in burst | Naïve | 13.4 ± 2.0 | 55.3 ± 9.1 | 48.9 ± 8.8 | 40.2 ± 7.3 | 42.9 ± 7.6 | 24.6 ± 6.7 | 28.0 ± 5.3 | 6.6 ± 2.0 |
|  | CCI | 14.2 ± 5.8 | 59.7 ± 4.5 | 48.8 ± 4.4 | 55.6 ± 5.0 | 54.1 ± 5.2 | 53.1 ± 8.0* | 46.9 ± 7.8* | 17.0 ± 3.8* |
|  | CCI+HFS | 8.9 ± 2.0 | 45.0 ± 7.2 | 33.5 ± 6.1 | 45.4 ± 5.2 | 42.1 ± 6.5 | 35.8 ± 8.0# | 29.4 ± 8.9# | 11.6 ± 2.9 |
| Mean interburst time (ms) | Naïve | 10147.7 ± 3829.2 | 401.0 ± 108.0 | 1646.3 ± 578.8 | 1836.9 ± 1109.8 | 477.7 ± 130.5 | 806.4 ± 171.8 | 627.4 ± 220.9 | 1881.9 ± 441.6 |
|  | CCI | 3221.3 ± 874.2 | 150.0 ± 19.6 | 726.4 ± 255.5 | 272.6 ± 75.8 | 189.0 ± 33.2* | 93.0 ± 27.5* | 130.8 ± 37.0* | 566.0 ± 186.3* |
|  | CCI+HFS | 2914.7 ± 755.2 | 400.2 ± 118.4 | 2979.5 ± 1153.9 | 382.6 ± 64.7 | 313.5 ± 65.3 | 393.8 ± 132.4# | 642.0 ± 320.4 | 1835.1 ± 707.2 |

PAIN MANAGEMENT

RELATED APPLICATIONS

This application is a continuation of, and claims priority under 35 U.S.C. §120 to, U.S. patent application Ser. No. 13/643,670 filed Nov. 20, 2012, and granted as U.S. Pat. No. 8,977,362, which is a national stage application, filed under 35 U.S.C. §371, of International Application No. PCT/US2011/034203 filed Apr. 27, 2011, which claims the benefit under 35 U.S.C. §119 of U.S. Provisional Application No. 61/328,583, filed Apr. 27, 2010, the entire contents of each are hereby incorporated by reference herein.

BACKGROUND

More than 11 million Americans report chronic pain as a significant disability. The financial burden of chronic pain in the United States alone is estimated at higher than $100 billion a year, including lost productivity and medical expenses. Viewed globally, there is a large underserved population for pain management medications and/or therapies.

Chronic pain is typically classified as pain lasting more than 6 months and generally divided into three main types: nociceptive, psychogenic or neuropathic (e.g., due to nerve injury) although the distinction between these types can be blurred. Especially true for chronic neuropathic pain, current treatment options including opioids and nonsteroidal anti-inflammatory drugs (e.g. COX inhibitors) are often ineffective, contraindicated or associated with significant gastrointestinal and cardiac side effects, sedation, respiratory depression, addiction and drug abuse. It is widely believed that pharmacotherapy, surgical ablation, and externally applied non-drug therapies (e.g. transcutaneous electrical nerve stimulation and acupuncture) have all reached a ceiling well below the desired level of patients and clinicians. Novel ideas are thus needed in pain research.

SUMMARY

The invention provides a solution to the long-standing problem of accurate identification of clinical pain and reliable therapeutic intervention to alleviate such pain. Chronic clinical pain includes neuropathic pain such as that associated with direct nerve damage, amputation, chemotherapy, diabetes, HIV infection or AIDS, Multiple Sclerosis, shingles, sciatic nerve compression or injury, as well as spine surgery.

Accordingly, a method of identifying a subject characterized as suffering from chronic pain, e.g., chronic neuropathic pain, is carried out by detecting a pain signature comprising an pattern of neuronal firing compared to a normal pattern of neuronal firing, e.g., a pattern obtained from a subject or a cohort of subjects that have been characterized as not suffering from pain. The pattern of firing is obtained from a single neuron or a plurality of neurons. The brain of a subject afflicted with chronic pain has stored a pain signature. The pattern comprises an elevated evoked response to stimuli, rhythmic after-discharge signaling, and/or increased spontaneous background firing. The pain and neuronal firing pattern subsists after an injury heals or is completely unrelated to a stimulus, e.g., an injury, or the degree of a stimulus. In one example, the pain signature comprises a pattern of neuronal burst-firing, each burst of the burst firing comprising at least 10 times, 50 times, 100 times or more, the number of spikes compared to a control non-pain pattern.

An exemplary pain signature comprises a pattern of burst-firing that is characterized by one or more of the following measurable parameters: (a) a maximum interval signifying burst onset (6 ms); (b) a maximum interspike interval (9 ms); (c) longest increase in interspike interval within a burst (2 ms); (d) a minimum number of spikes within a burst (2). An aberrant pattern or pain signature is further characterized by a spontaneous high frequency rhythmic oscillation of long epoch.

A method of preventing or reducing pain perception involves identifying a subject using the criteria described above and administering to the subject at least one electrical pulse to the subject, the electrical pulse being at least about 100, 150, or 200 Hz, between about 1 and about 3 volts, between about 1 and about 3 milliampere, and between about 0.25 and about 1 second in duration. Rather than stimulating the aberrantly firing neurons back to a recovery pattern, the electrical pulse of at least about 100 Hz jams or halts the pain circuitry at the level of the source. Subjects to be diagnosed and/or treated include human patients as well as animals such as companion animals (e.g., dogs, cats) as well as livestock and performance animals (e.g., horses, cattle, and the like).

The invention includes an anatomically-based and neurotechnology-oriented pain therapy system to achieve neuromodulation of specific brain regions, for example using transcutaneous magnetic fields or chronically implanted electrodes. In general, in an aspect, the invention provides a system including a processor configured to be coupled to an electrical lead that is configured to sense electrical activity in a patient, a memory coupled to the processor, the memory containing computer readable instructions that, when executed by the processor, cause the processor to detect a pain signature in the sensed electrical activity, determine a treatment protocol in response to the detected pain signature, and cause the treatment protocol to be delivered to the patient via the electrical lead.

In general, in another aspect, the invention provides a system including a processor configured to provide an electrical treatment protocol to a patient, the electrical treatment protocol being configured to treat chronic pain in the patient, the treatment protocol including providing at least one electrical pulse to the patient, the electrical pulse being at least about 150 Hz, between about 1 and about 3 volts, between about 1 and about 3 milliampere, and between about 0.25 and about 1 second in duration.

In general, in a further aspect, the invention provides a method of identifying a subject comprising chronic pain, including detecting a pain signature comprising a pattern of neuronal firing, said pattern comprising an elevated evoked response to stimuli, rhythmic after-discharge signaling, and increased spontaneous background firing.

In general, in still another aspect, the invention provides a method of identifying a subject comprising chronic pain, comprising detecting a pain signature comprising a pattern of burst-firing, each burst of said burst firing comprising at least 10 times the number of spikes compared to a control non-pain pattern.

In general, in yet another aspect, the invention provides a method of identifying a subject comprising chronic pain, comprising detecting a pain signature including a pattern of burst-firing, wherein said pattern comprises burst-firing, said burst firing including (a) a maximum interval signifying burst onset (6 ms), (b) a maximum interspike interval (9 ms), (c) longest increase in interspike interval within a burst (2 ms), or (d) a minimum number of spikes within a burst (2).

In general, in an even further aspect, the invention provides a method of preventing or reducing pain perception, comprising identifying a subject, and administering to said subject at least one electrical pulse to the subject, the electrical pulse being at least about 150 Hz, between about 1 and about 3 volts, between about 1 and about 3 milliampere, and between about 0.25 and about 1 second in duration.

Various aspects of the invention may provide one or more of the following capabilities. The efficiency, battery life, and device life of devices used for neurostimulation can be improved over prior techniques. More physiologically relevant brain structures can be targeted compared with prior techniques. Side effects can be reduced compared with prior techniques. The temporal and overall amount of delivered current can be reduced compared with prior techniques. The likelihood of excessive tissue exposure, which has been thought to cause long-term changes and side effects, can be reduced compared with prior techniques. The necessity for combined pharmacologic intervention can be reduced, or possibly eliminated compared prior techniques. Chronic pain can be empirically diagnosed.

These and other capabilities of the invention, along with the invention itself, will be more fully understood after a review of the following figures, detailed description, and claims. Other features and advantages of the invention will be apparent from the following description of the preferred embodiments thereof, and from the claims. All references cited herein are incorporated by reference.

BRIEF DESCRIPTION OF THE DRAWINGS

FIG. 13 is a graphical representation showing neuronal activity from a single unit in the thalamus (VPL) with receptive field in the injured hindpaw one week after CCI. Note distinct firing pattern associated with CCI and emergence of spontaneous high frequency rhythmic oscillation of long epoch (~) after pinch. The high spontaneous rate of firing is only briefly interrupted by application of lidocaine (4%) directly on the dorsal surface of the spinal cord at upper thoracic level, whereas evoked responses to brush and pinch disappear. Note sustained and more elevated spontaneous firing within seconds after lidocaine application, indicating a phenomenon independent of peripheral or caudal input from the spinal cord (i.e. inherent within the brain).

FIG. 14 is a drawing and a photograph of rodent into which microelectrodes were implanted in the brain with tips located in the VPL nucleus of the thalamus. Signal generated from these electrodes (RE) was relayed to a data acquisition system via a head stage fixed to the skull of the animal. Neuropathic pain was measured behaviorally and induced by chronic constriction injury (CCI) of the sciatic nerve, a 'mixed' nerve that receives sensory input from the leg and connects with central nervous system (CNS) circuitry projecting into the VPL. To evoke thermal nociception, a laser beam was focused on the plantar hindlimb to illicit a withdrawal behavior of measurable latency.

FIG. 15 is a photograph of a modified microelectrode design. Electrode segments were fused together with Epoxy resin in order to form a respective cathode and anode during DBS trials. The Teflon coating was cut to reveal 0.5 mm of silver wire on each electrode. Cathode and Anode are separated by 1 mm from tip to tip as shown.

FIG. 16 is a photograph of a recording setup. Following craniotomy, the microelectrode was lowered to a depth of 5-6 mm until an appropriate VPL unit was isolated for recording.

FIG. 17 is an illustration of the relative position of the bipolar stimulating electrodes in relation to the VPL, and the area directly affected by stimulation (shaded) based on several modeling studies (refer to text).

FIG. 18A shows representative examples of tonic firing in two units under naïve and CCI conditions. Note increased rate of spontaneous firing and firing evoked by pressure (Pr), pinch (Pi) and afterdischarge (AD) in CCI rat compared to naïve. FIG. 2B shows mean rate of firing in two groups of VPL neurons in naïve and CCI rats (n=9-11/gr).

FIG. 19A shows a representative example of spontaneously rhythmic oscillation (grey shade), which was abolished after complete spinal transection (arrow, asterisk indicates absence of a response to brush after transection). Rhythmic oscillation was observed in 3/9 (33%) neurons in rats with CCI. FIG. 19B shows phase histograms during rhythmic oscillation fitted with a sine wave curve (before spinal transection, left panel). Note elimination of oscillation after transaction reflected by a much lower amplitude sine wave (right panel). FIG. 19C shows sine wave parameters in neurons with oscillation fitted to phase histograms.

FIGS. 20A-B are line graphs showing representative examples of the effect of HFS (100 Hz) and LFS (25 Hz) on the firing rate of two VPL neurons in two rats with CCI. HFS attenuated all evoked activity and afterdischarge, whereas spontaneous firing remained unchanged. Note increasing effects with incremental increases in voltage, compared to lack of prominent effect using LFS. FIGS. 20C-D are graphs showing mean percent change in firing rates after HFS (n=9 units) or LFS (n=5 units) compared to pre-stimulation baselines for each unit. HFS significantly inhibited all evoked responses and after discharge in units recorded from CCI rats, except spontaneous activity, in contrast to LFS which had no significant effect.

FIG. 24A shows mean withdrawal latencies before and after CCI (n=5 rats). Pre-CCI values represent average withdrawal latencies in both hindpaws which were not significantly different, whereas post-CCI latency was significantly decreased in ipsilateral (injured) hindpaws compared to contralateral (uninjured) hindpaws, indicating thermal hyperalgesia. FIG. 24B shows the effect of HFS (arrows) on withdrawal latencies in ipsilateral and contralateral hindpaws (arrowhead denotes sham condition, i.e. connecting the stimulating electrodes to the stimulator without applying voltage). FIG. 24C shows mean withdrawal latencies 5 min before HFS and at 5 and 10 min after HFS showing significant increase in latency 5 min after HFS (n=4 rats), suggesting attenuation of hyperalgesia.

FIG. 26A shows that relatively 'moderate' microstimulation (100 HZ, 0.5 V, 1 s duration pulse) resulted in a significantly decreased firing evoked by pressure and pinch as well as afterdischarge (n=4 out of 9 neurons). FIG. 26B shows that HFS decreased the firing rate in naïve rats, reaching significant levels for all firing modalities except for the weakest von Frey filament stimulation (0.6 g) and afterdischarge (n=6 units).

FIG. 28 is a series of photographs and a bar graph. Chronic microelectrode implant had no effect on the mean ratio of OX-42 or GFAP immunofluorescence intensity in the vicinity of stimulating electrode tips, suggesting limited or absent glial activation or reactive gliosis (n=4 rats).

FIGS. 29, 29A, and 29B are a series of tables (Table 1, Table 2, Table 3, Table 4).

Spontaneous activity is followed by increased activity evoked by brushing of the receptive filed in the injured paw (t=19-40 s).

Figure 34:
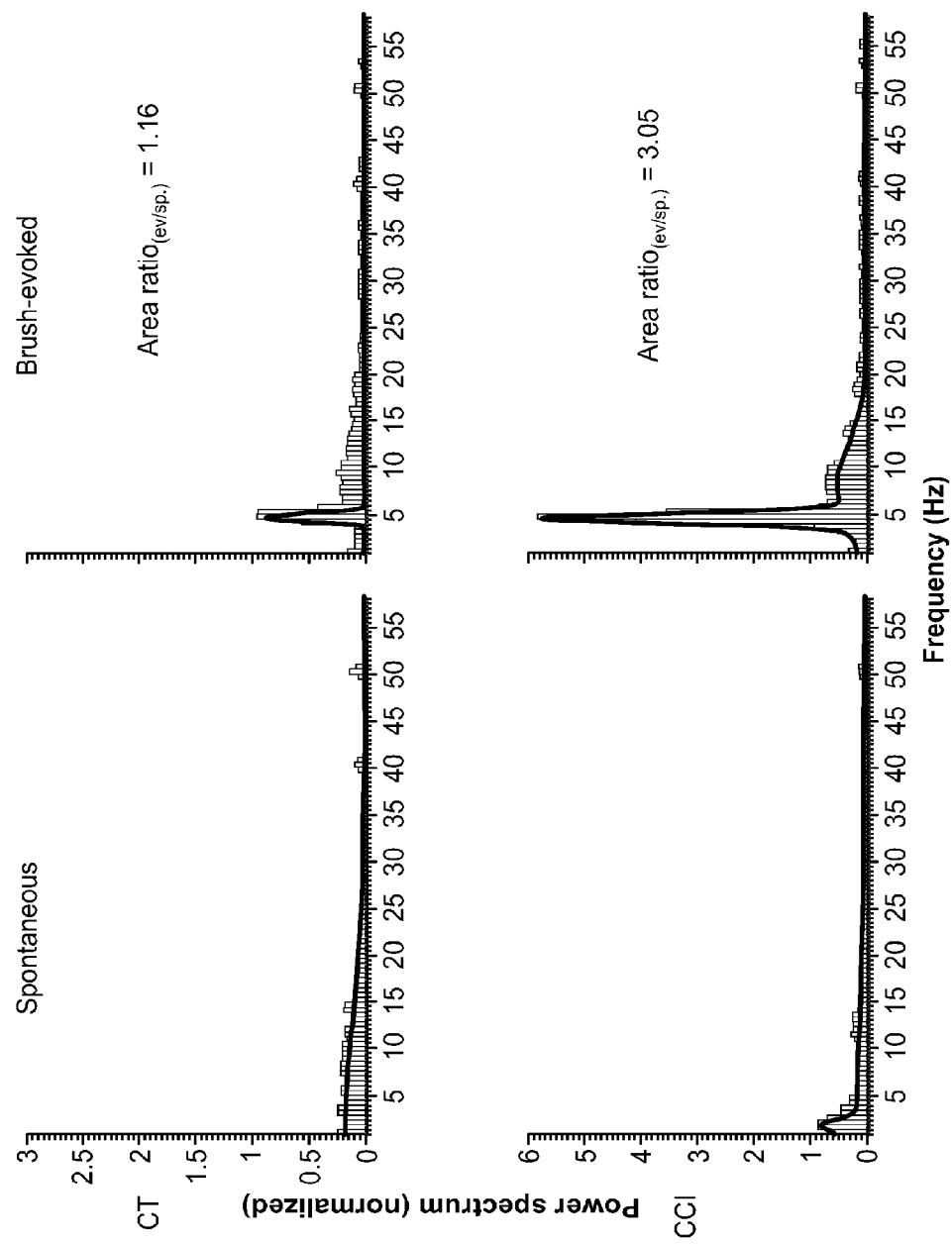

FIG. 34 is a series of graphs showing spontaneous activity and activity in response to brushing of the contralateral paw. Spectral power was computed using FFT analysis of the recorded signal from the VPL bilaterally and normalized for each VPL. A broad peak (1-15 Hz) was observed under spontaneous conditions in CT, which more prominently shifted leftwards (1-3 Hz) in CCI. During evoked responses, the peak at around 5 Hz was more prominent in CCI compared to CT, with a broader power distribution in the higher-frequency (5-15 Hz) region. Overall power was increased bilaterally during evoked responses to brush; however, this increase was almost 3 folds higher in CCI (note increased evoked/spontaneous ratio of area power from 1.16 in CT to 3.05 in CCI). Red plots represent Gaussian data fit.

Figure 35:
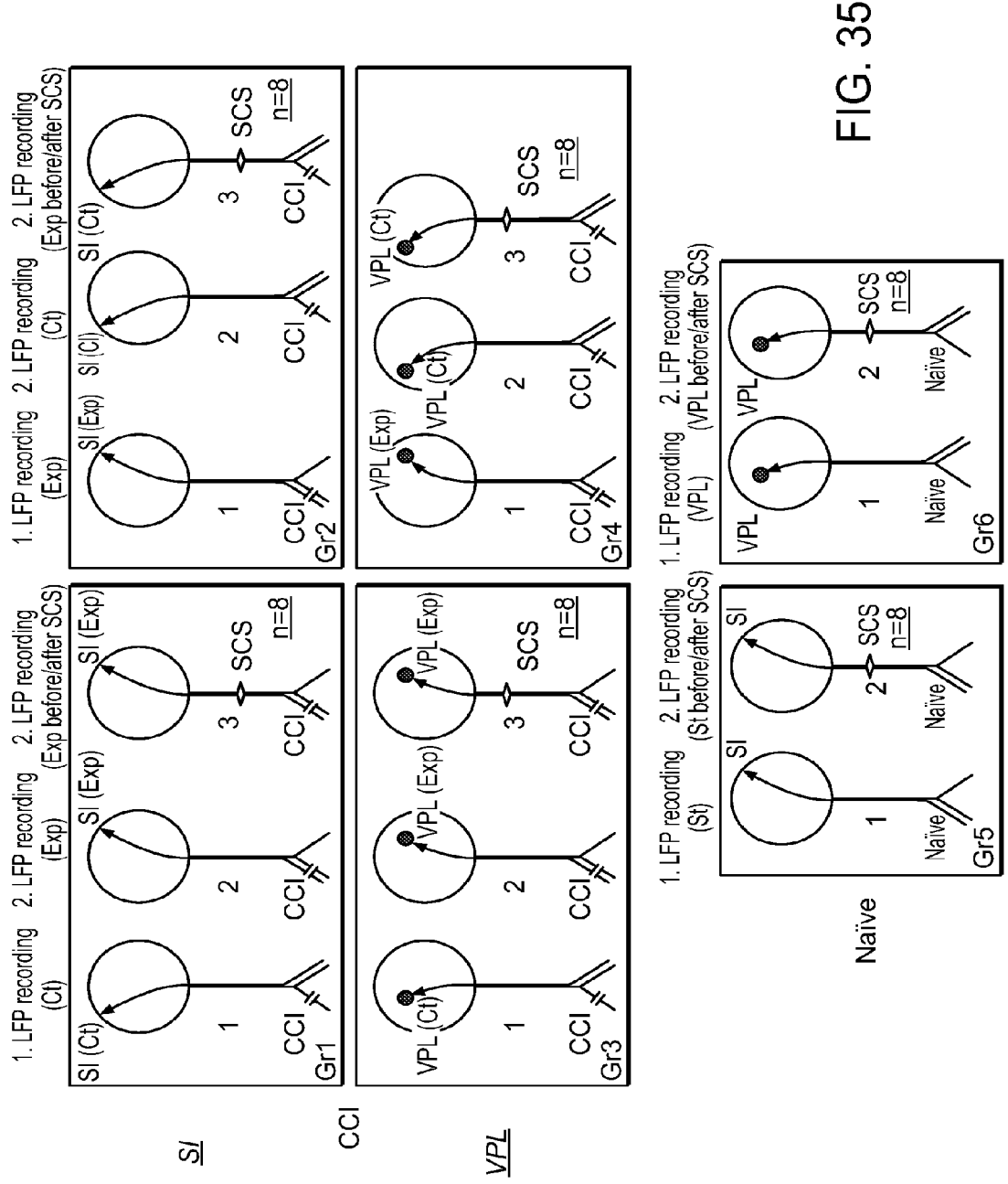

FIG. 35 is a series of illustrations depicting LFP recordings of the six groups (Gr, n=8/Gr, total 48 rats; Exp: Experimental, Ct: Control):

Gr 1: Record LFP in somatosensory cortex (SI) first ipsilateral (Ct) then contralateral (Exp) to CCI before/after SCS.

Gr 2: Record LFP in SI first contralateral (Exp) then ipsilateral (Ct) to CCI before/after SCS.

Gr 3: Record LFP in VPL first ipsilateral (Ct) then contralateral (Exp) to CCI before/after SCS.

Gr 4: Record LFP in VPL first contralateral (Exp) then ipsilateral (Ct) to CCI before/after SCS.

Gr 5: Record LFP in SI in naïve before/after SCS.

Gr 6: Record LFP in VPL in naïve before/after SCS.

DETAILED DESCRIPTION

Chronic pain is a serious challenge in terms of pathophysiology, diagnosis, therapy and social burden. Studies in humans and laboratory animals suggest a relationship between intractable pain and ectopic neuronal activity in thalamic and cortical areas, leading to dysfunctional connectivity in the brain's 'pain network'. Contributing to this network are dense interconnections between thalamic and cortical modules whose interactions are being investigated in terms of directionality and temporal dynamics. In humans, intracranial electrode recordings demonstrate altered neuronal activity within these networks in patients with chronic pain. Single-cell electrophysiology and magneto-encephalographic (MEG) studies further support the hypothesis of thalamo-cortical dysrhythmia (TCD) in patients with complex regional pain syndrome, whereas, interestingly, imaging studies show cortical thinning under chronic pain conditions. Similar physiological results were found using animal models of pain, thus allowing for more detailed mechanistic analysis, whereby a series of studies have validated the pathophysiology of thalamo-cortico-thalamic circuitry.

Rather than being the symptom of a disease process, chronic pain is itself a disease process. Chronic pain is unrelenting and not self-limiting and as stated earlier, can persist for years and even decades after the initial injury. If not treated, chronic pain can lead to anxiety, fear, depression, sleeplessness and impairment of social interaction. Chronic, non-malignant pain is predominately neuropathic in nature and involves damage either to the peripheral or central nervous systems.

Nociceptive and neuropathic pain are caused by different neurophysiological processes, and therefore respond to different treatment modalities. Nociceptive pain is mediated by receptors on A-delta and C-fibers which are located in skin, bone, connective tissue, muscle and viscera. These receptors serve a biologically useful role at localizing noxious chemical, thermal and mechanical stimuli. Nociceptive pain can be somatic or visceral in nature. Somatic pain tends to be well localized, constant pain that is described as sharp, aching, throbbing, or gnawing. Visceral pain, on the other hand, tends to be vague in distribution, paroxysmal in nature and is usually described as deep, aching, squeezing and colicky in nature. Examples of nociceptive pain include: postoperative pain, pain associated with trauma, and the chronic pain of arthritis. Nociceptive pain often responds to opioids and non-steroidal anti-inflammatories (NSAIDS). Neuropathic pain, in contrast to nociceptive pain, is described as "burning", "electric", "tingling", and "shooting" in nature and can be unrelated to a stimulus such as an injury. Examples of neuropathic pain include: monoradiculopathies, trigeminal neuralgia, postherpetic neuralgia, phantom limb pain, complex regional pain syndromes and the various peripheral neuropathies. Neuropathic pain tends to be only partially responsive to opioid therapy.

As is discussed above, chronic pain is a significant clinical problem. Most potent treatment is opiate derivatives; however, these drugs are associated with serious side effects. Moreover, one type of chronic pain, neuropathic pain (due to direct damage to the nervous system (peripheral nerves, spinal cord or brain)) is usually resistant to treatment. During peripheral neuropathic pain, the degree of pain is often unrelated to the degree of tissue damage at the site of nerve injury. Clinical data indicate abnormal activity pattern in patients with chronic pain, particularly in the sensory thalamus (ventroposterior lateral; VPL), a major nuclear relay for sensory information.

Chronic abnormal sensations (sensory neuropathies) following peripheral nerve injury are caused by long-term changes in brain activity patterns. Sensory neuropathies and abnormal brain patterns are reversible with direct intervention in the brain by deep brain stimulation (DBS).

The data described herein was generated using an art-recognized pre-clinical rat model of peripheral neuropathy (chronic constriction injury, CCI). The brain area studied was in the sensory thalamus (ventroposterior lateral; VPL), a major nuclear relay for sensory information. The VPL on one side of the brain receives sensory input from the contralateral side of the body (neurons in the VPL contralateral to CCI were studied). Neuronal activity from single neurons in the VPL was recorded in live animals under deep anesthesia as extracellular action potentials. Neuronal patterns recorded were either evoked by stimuli on the corresponding receptive field in the body or spontaneous (no stimulation of the receptive field). Sensory neuropathies were tested using standard behavioral measurement of thermal sensitivity to a heat stimulus (latency of withdrawal to moderately noxious heat) in awake, unrestrained, non-anesthetized rats. For reversal of abnormal activity patterns, DBS was delivered in the VPL under deep anesthesia during recording. For reversal of thermal hypersensitivity, DBS was delivered in the VPL in awake, unrestrained, non-anesthetized rats.

In rats with neuropathic injury, abnormal neuronal activity was recorded in the VPL contralateral to CCI (similar results were confirmed in another model of peripheral neuropathy by spinal nerve ligation; SNL). The neuropathy-induced abnormal activity in all rats included hyperexcitability of evoked responses, emergence of high spontaneous firing and aberrant evoked burst (in addition to occasional spontaneous rhythmic firing in some rats). Abnormal neuronal activity occurred exclusively in neurons with receptive fields in the leg (supplied by the injured sciatic nerve). Neuronal activity recorded from the VPL with receptive fields beyond the injured leg, and those from the ventrolateral medial (VPM) nuclear group (which receives major input from the face), were not different from those in naïve rats. Tissue collected from neuropathic rats (postmortem) showed local neuroinflammation in the VPL contralateral to CCI. DBS reversed all abnormal patterns of neuronal activity in the VPL (except spontaneous discharge, which remained high in neuropathic rats), with no side effects. DBS reversed thermal hyperalgesia in neuropathic rats, with no side effects.

Pain Signature

The neuronal activity patterns that make up the pain signature can be divided into two major categories: spontaneous and evoked. Spontaneous activity is further divided between baseline activity (on-going spontaneous discharge in the absence of overt bodily stimuli) and afterdischarge (on-going spontaneous discharge immediately following the cessation of a noxious bodily stimulus). Evoked activity is further divided between activity in response to noxious (e.g. painful high pressure or pinch) or non-noxious stimuli (e.g. gentle touch or brush). To make use of the 'signal' (i.e. for the sensory to detect it reliably), the signal could be either detected in an autonomous 'rigid' manner (device with pre-programmed fixed set of parameters), an autonomous 'flexible' manner (device capable to 'learning', i.e. with capacity to correct for errors to improve reliability of accurate detection), or recognized by outside observer (experimenter, healthcare practitioner or self in the form of Biofeedback).

One way of objectively or empirically quantifying the signature is by computing the rate of firing (i.e. number of action potentials in time) for individual neurons. The data show, for example, that the firing rate during pinch under pain conditions is higher compared to normal. One point to consider is that, for example, the firing rate during pressure under pain conditions is lower compared to that during pinch under normal conditions. Thus relying on firing rates exclusively to distinguish normal from pain states will not suffice to program an automated detector, unless advance or real-time knowledge of the stimulation state is obtained. Though burst characteristics are based on parameters different than firing rate (e.g. number of bursts, mean spikes/burst), the same argument also applies (overlapping data between spontaneous and evoked activities).

In spite of these apparent limitations, one alternative is to consider a real-life example. Evoked noxious events are rare throughout an individual's daily activities, including those with chronic pain. Such events are usually the result of infrequent injuries sustained from falling or projectiles. Therefore, the category of activity evoked by noxious stimuli could be ignored (including noxious heat, and consequently, including afterdischarge). A major category of activity throughout daytime is predominately evoked by light touch, secondary to gentle touch such as clothing, tapping, 'feeling', etc. A second major category is spontaneous activity. Of note, pressure and pinch-evoked activities under pain conditions are exceedingly higher than any other type of activity under normal or pain condition, constituting a 'safety margin' for programming. If noxious events do occur, they would be interpreted as exceeding a set limit for 'pain touch' anyhow, and the period of afterdischarge would fall within the therapeutic time window and would therefore be prevented. Furthermore, the difference between spontaneous and pressure or pinch-evoked activities is exceedingly high, therefore allowing for the setting of 2 distinct zones of activities termed 'normal' or 'pain', respectively.

Another option for the design of a closed-loop device to detect pain signature, based on firing rate, is to couple the device to a mechanical sensing probe on the affected area of the body (superficially on the skin) capable of detecting mechanical energies such as touch, pressure and pinch stimuli, as well as thermal energies such as hot/cold surfaces, and relay this information to the closed-loop device in parallel to the main neuronal detector of the brain signature. Such a design would enable an automated response while lessening the need for an observer or feedback from the subject to classify the type of neuronal activity (i.e. spontaneous or evoked).

Other types of neuronal activities are also envisioned for the detection of the signature. These include neuronal activity recorded directly or indirectly at the level of Local Field Potential (LFP: i.e., sampling from a neuronal population) detecting shifts in power spectra using Fourier type analysis, absence or emergence of new spectral peaks), electroencephalogram (EEG), magnetoencephalogram (MEG), in addition to other types of imaging techniques and brain scans (for example Magnetic Resonance Imaging, MRI and fMRI and Positron Emission Tomography or PET, etc.)

Sensor Design

The sensor part of the closed-loop device for pain management, or an open loop sensor device for pain diagnosis, depends on the capability of the sensor to record neuronal activity (from single neurons or a population of neurons, directly or indirectly using surrogate measurements such as blood flow or volume). Such pain signature manifests high temporal and special resolutions, as the said neuronal activity is generated by a specific population of neurons in the brain (hence close proximity of the probe is needed for specific detection of the electric signal), and that the activity pattern or changes thereof occurs mostly in the order of milliseconds or seconds. While current technology allows such high temporal and special resolutions using implantable microelectrodes, the use of other 'sensor' technologies, in particular non-invasive EEG functional imaging is useful.

More importantly, design strategy considers the possibility of not only recording from a single area or structure in the brain, or looking at multiple areas or structures in the brain individually, but also studying the interaction between these regions under normal and pathological or pain conditions, as it is known that network connectivity in the brain is altered in chronic pain patients. Dysfunctional network connectivity will manifest by combined temporal and spatial analysis of neuronal activity among more than one brain area or structure at any of the recording or detection levels discussed above.

Stimulation Design

A closed-loop device is programmed to detect the pain signature and operate upon detection of such signals to send a command to an operator that would deliver therapy with the aims of reversing the signature. For example, this device would be turned ON in wakeful states and OFF during sleep, depending on condition severity and need. Furthermore, the device is optionally set to deliver a therapeutic pulse periodically or intermittently (e.g., every 2 hrs).

Clinical Application

In addition to being used for analgesia (decreasing existent pain), the device is used for anesthesia during invasive or surgical procedures, in particular if anesthetics or sedatives are contraindicated. More importantly, the diagnostic aspects of the device are useful in cases where subjects or patients are non-cooperative, unable to respond, cognitively impaired, facing language barrier, or where simply verbal reporting is unreliable (e.g., in the pediatric population or with adult drug-seekers).

Deep Brain Stimulation

Embodiments of the invention provide techniques for developing a safe, effective and long-term treatment strategy for persistent pain using, for example, deep brain stimulation (DBS) for the relief of chronic pain. The techniques can include measuring electrical activity in a patient's brain to determine if a certain pain signature exists. This can involve the use of, for example, electrodes implanted into a patient's brain. The technique can also include providing therapeutic electrical stimulation to, for example, the brain of the patient at predefined times, frequencies, voltages, periodicities, and currents. The electrical stimulation can be provided in response to detecting the presence of the predefined pain signature in the patient in a closed-loop design, or can be provided on a periodic basis in a open loop system (e.g., every 1-2 hours). Other embodiments are within the scope of the invention.

One embodiment includes the use of a closed-loop design that can enable neurostimulation to be triggered upon detection of, for example, abnormal neuronal activity linked to (or immediately preceding) pain episodes, thus reversing aberrant neuronal activity and attenuating (or even preventing) pain, without interfering with 'normal' brain activity. An additional benefit can also be the delivery of high frequency current (e.g., >150 Hz) that blocks (or 'jams') neuronal firing with no reported side effects.

Anatomically, a major relay station to ascending sensory information is preferably targeted in the thalamus, based on empirical evidence showing a characteristic burst firing pattern recorded from the thalamus of awake patients with neuropathic pain, which closely resembles that recorded from the thalamus of animal models of neuropathic pain. To this end, it has been 1) identified a thalamic neuronal activity pattern associated with neuropathic pain in anesthetized rats ('pain signature'); 2) determined an optimal stimulation protocol that reverses pain-related thalamic firing; 3) achieved reversal of pain-related behavior by neurostimulation.

A series of stimulation protocols have been tested and several have been identified that best achieve reversal of pain-related neuronal activity with the least amount of current delivered in duration and intensity. High frequency stimulation (e.g., >150 Hz) can 'jam' neuronal circuitry, resulting in 'lesion' effects that are reversible. The brain circuitry targeted would preferably be the pain circuitry directly, mainly the sensory thalamus. The data show that a brief pulse train at high frequency typically effectively attenuates neuronal hyperexcitability in thalamic neurons associated with chronic pain, and attenuates pain behavior.

A neuronal activity pattern has been characterized in thalamic neurons that is associated with chronic pain. The rationale for choosing thalamic neurons is at least partially based on tests showing that thalamic sensory neurons typically undergo distinctive plasticity changes under conditions of spinal cord injury-pain, and that reversal of these plastic changes by pharmacologic treatment is linked to reversal of pain behavior. In support of this, data suggest that thalamic sensory neurons with receptive field in the dermatome of the injured sciatic nerve (a model of neuropathic pain) undergo distinct changes, including hyper-responsiveness to peripheral stimuli, increased spontaneous firing and increased probability of afterdischarge. In addition, these experiments have been validated in awake un-anesthetized rats, and tested the anti-nociceptive effects of neurostimulation on nociceptive behavior in a rat model of chronic pain.

Figure 1:
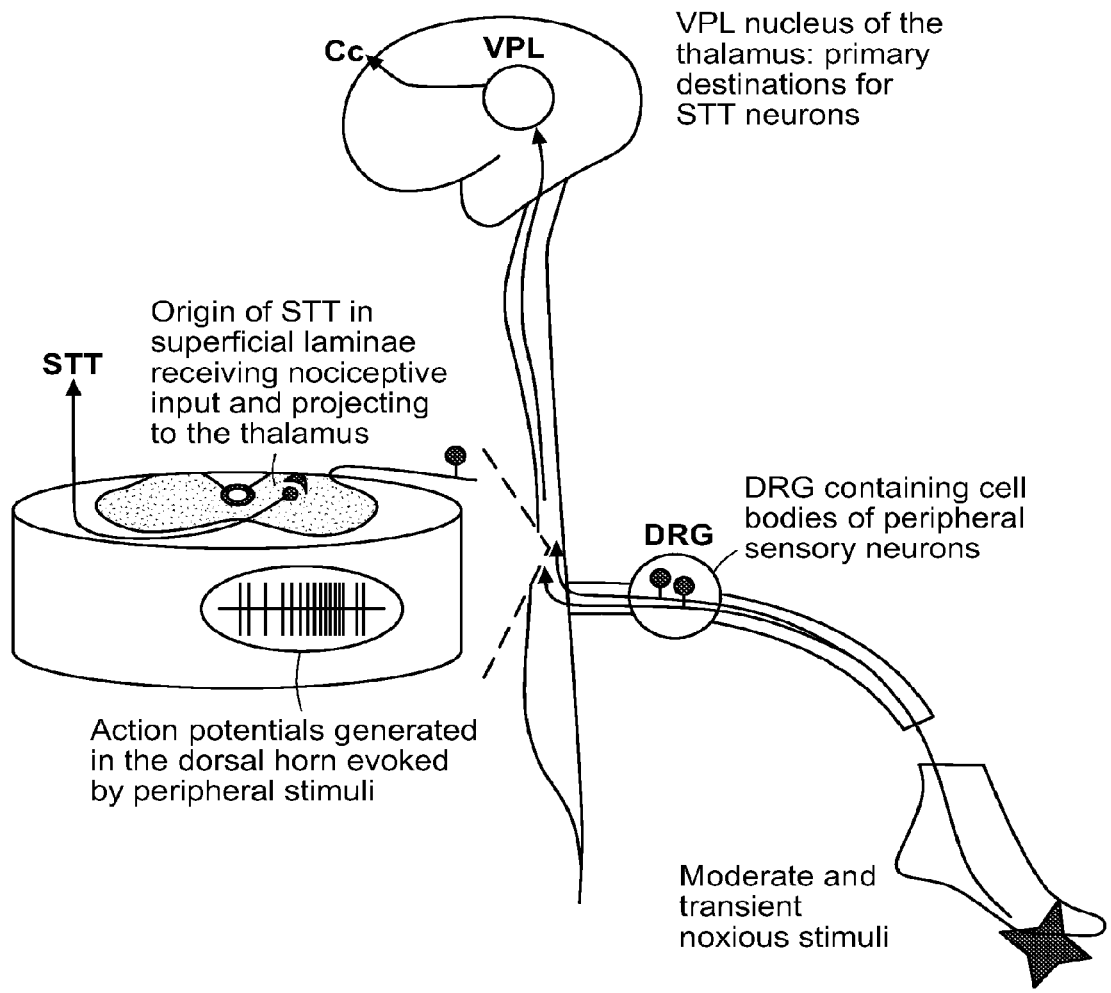
FIG. 1 is a diagram of a classic 'pain pathway' illustrating the spinothalamic tract (STT) and how nociceptive information is transmitted from the periphery via the dorsal root ganglion (DRG) to central structures including the ventroposterior lateral (VPL) nucleus of the thalamus to the cerebral cortex (Cc).

During normal nociception (e.g., FIG. 1), information about stimulus location and intensity is encoded in precise patterns of action potential firing. Individual neurons produce, and dynamically switch between, a multitude of discrete firing modes such as single spikes, bursts (e.g., which can be configured in a variety of ways given differences in timing and patterning), spindle waves and spike motif trains termed 'epochs.' Firing patterns are a product of (and influence) neurons in directly wired local circuits and in widely distributed circuits. One such circuit element, the thalamus, serves as an important sensory relay to higher cortical circuits.

An overall increase in thalamic gain is associated with an increased transfer ratio at the thalamocortical synapse that serves to more potently activate cortical circuits involved in pain sensation. In other brain areas, for example in the visual system, the information content of bursts is typically higher than single spikes. In the hippocampus, the probability of generating at least one postsynaptic spike is higher for bursts than for single spikes. Thalamic nociceptive neurons undergo spontaneous firing activity in normal human subjects and rats, conferring distinct neuronal rhythmicity (oscillations) at defined resonant frequencies. Temporal coincidence of such activity patterns with cortical activity mediates functional states that characterize sensory experiences. Several neurological conditions can upset this temporal coincidence, and abnormal thalamic activity has been linked to chronic painful conditions. For example, spinal cord injury-induced pain behavior is associated with a higher prevalence of spontaneous burst firing in the ventroposterior lateral (VPL) nucleus of the thalamus, in addition to an increased number of neurons with oscillatory firing pattern; burst intervals are more regular, between-event intervals are longer and burst events contain more spikes.

Rhythmic network oscillation in the thalamus is modifiable by thalamic events and external synaptic input. En passant axons of thalamocortical, in addition to corticothalamic, relay neurons receive tuning from the surrounding nucleus reticularis feedback circuit that could be reconfigured after injury to the nervous system. Unstable or aberrantly processed nociceptive inputs lead to abnormal generation or amplification of nociceptive information. Therefore, neuromodulation by neurostimulation is an effective strategy to treat and/or manage chronic pain.

Thus, in view of the foregoing, a therapeutic system comprises the following: 1) a detector linked to a stimulator in a closed-loop device to detect and reduce abnormal brain activity, thus attenuating pain in an automated way; 2) a biocompatible closed-loop neurostimulation device specific for chronic pain, 3) surgical brain implant and testing of the device, and 4) clinical application for chronic pain treatment.

Figure 2A:
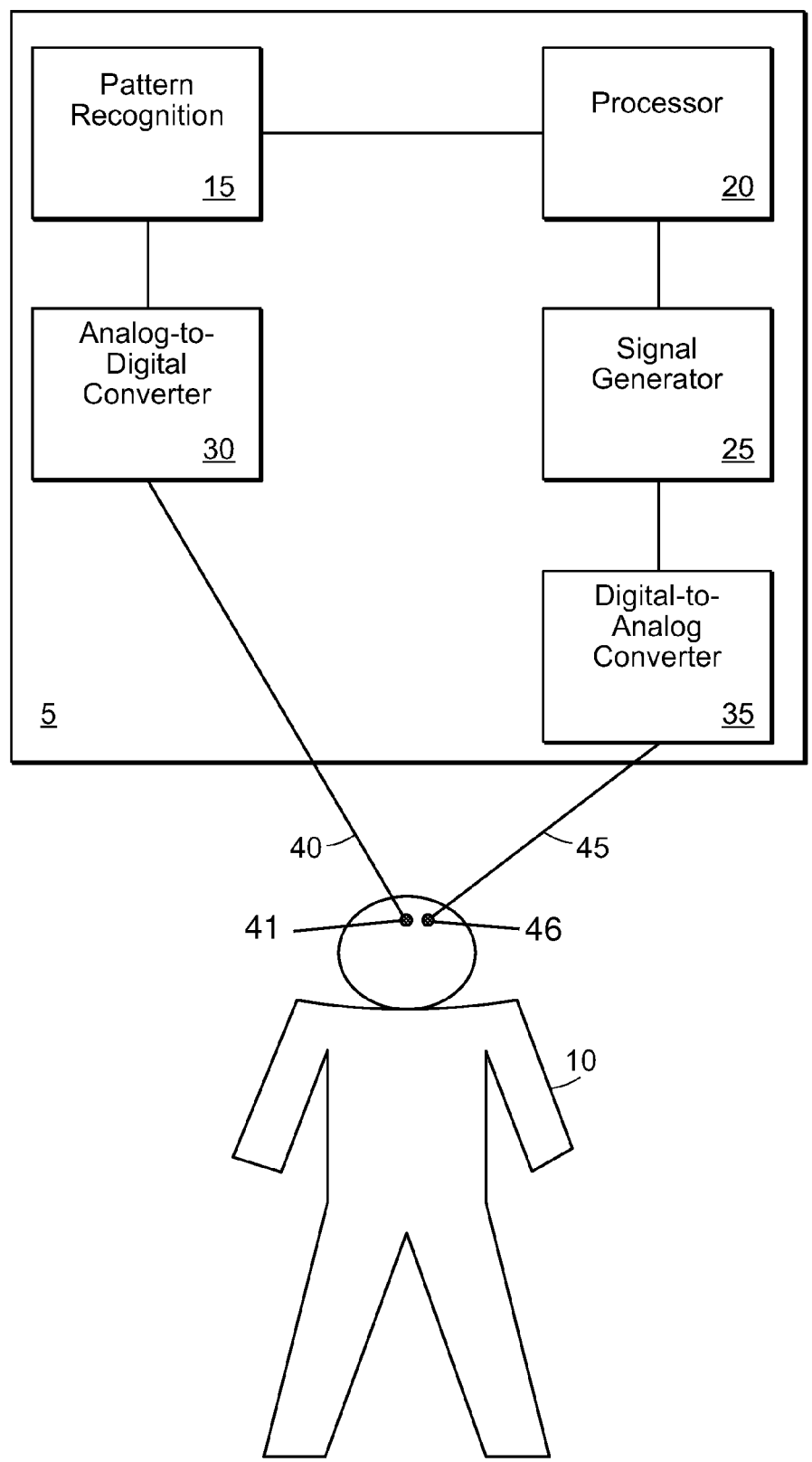
FIG. 2A is a diagram of a deep brain stimulation (DBS) system.
Figure 2B:
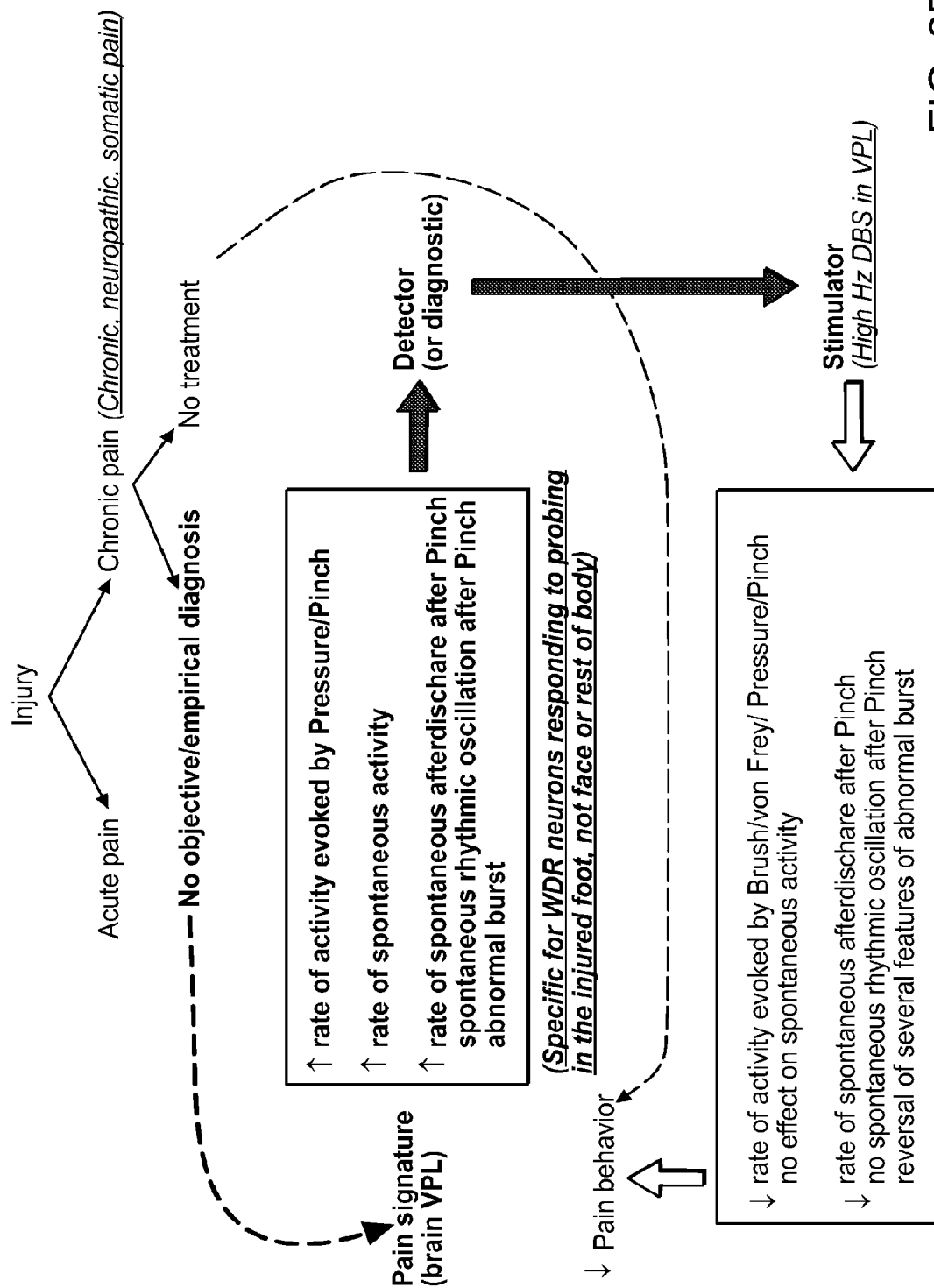
FIG. 2B is a flow diagram showing a diagnostic protocol for pain.

Referring to FIG. 2A, a deep brain stimulation (DBS) system 5 for use with a patient 10 is shown. Preferably, the DBS system 5 includes a pattern recognition system 15, a processor 20, a signal generator 25, an analog-to-digital converter 30, and a digital to analog converter 35. While the DBS system 5 is shown in FIG. 2A as including separate discrete blocks (e.g., 15, 20, 25, 30, and 35), other configurations are possible. For example, the functionality of one or more of the blocks 15, 20, 25, 30, and 35 can be combined into a single device and/or routine. Furthermore, while FIG. 2A includes a number of discrete blocks (e.g., 15, 20, 25, 30, and 35), certain blocks may be omitted in some configurations (e.g., pattern recognition system 15 and analog-to-digital converter 30 can be omitted in non-closed loop systems).

The analog-to-digital converter 30 is configured to receive signals from the brain of the patient 10 via an electrical lead 40 operably coupled to an electrode 41, and/or any other device that can measure neuronal activity (e.g., functional scanners). The electrical lead 40 can be configured to be implanted intracranially in the brain of the patient 10, although, the electrical lead 40 can be configured to measure electrical activity of the patient 10 in other areas (e.g., the VPL, hippocampus, and/or brain stem). Preferably, the electrical lead 40 is configured to be attached and/or in close proximity to a wide dynamic range (WDR) neuron in the brain of the patent 10, although other neurons can be used. Preferably, the WDR neuron is chosen as a function or psychological correlate of chronic pain being felt by the patient 10. For example, the WDR neuron chosen can correspond to the portion of the body which the patient 10 feels chronic pain (e.g., a neuron corresponding to the right leg of a patient suffering from chronic pain in their right leg, technically defined as a "receptive field"). The electrical lead 40 is configured to detect electrical activity in the brain of the patient 10, and to relay the sensed information to the system 5. Preferably, upon receiving sensed information from the electrical lead 40, the analog-to-digital converter converts the signal into a form desired by the pattern recognition system 15.

The pattern recognition system 15 is configured to monitor the signal provided by the electrical lead 40 to determine the presence of specific neuronal activity associated with chronic pain (e.g., the pain signatures identified in the exemplary data described herein). For example, the pattern recognition system 15 can be configured to detect an increase in spontaneous background firing, an increase in rate of firing evoked by external stimulus (e.g., pressure or pinch), rhythmic after-discharge signaling, rhythmic oscillation, abnormal bursting, etc. Preferably, electrical lead 40 is configured to detect neuronal activity (e.g., a pain signature) in the sensory thalamus (ventral posterolateral, VPL) of the brain of the patient 10. The pattern recognition system 15 can be configured to detect at least two different major types of neuronal activity spontaneous and evoked. Spontaneous activity is typically independent or temporally not associated with the presentation of an overt stimulus or identifiable cause. Spontaneous activity can best be described as an increase in the rate of spontaneous activity in pain subjects compared to naïve/normal. Evoked activity is typically activity correlated with an overt stimulus or identifiable cause. Evoked activity can best be described as an increase in the rate of evoked activity in pain subjects in response to peripherally applied noxious and non-noxious cutaneous stimuli compared to naïve/normal. In addition, abnormal bursting activity can occur during both spontaneous and evoked firing in pain compared to naïve/normal.

The pattern recognition system 15 is configured to communicate with the processor 20, and is configured to provide information to the processor 20 in a predetermined format over a network connection (e.g., a bus or network connection in embodiments where the pattern recognition system 15 is separate from the processor 20). The pattern recognition system 15 can be configured to perform various signal processing functions on the signals sensed from the patient 10 (e.g., frequency analysis, Fourier transform, inverse Fourier transform, filtering, de-noising, threshold analysis, analysis of interspike intervals, analysis of burst cycle periods, analysis of spikes within bursts, etc.).

The processor 20 can be configured to examine information provided by the pattern recognition system 15 to determine the appropriate response. For example, the processor 20 is configured to differentiate between various patterns that can be recognized by the pattern recognition system 15 and to determine an appropriate response. The processor 20 can differentiate between multiple recognized patterns, and determine an appropriate response strategy using, for example, a look-up table. The appropriate response can be nothing at all, or, for example, can be to cause an electrical signal to be provided to the brain of the patient 10 via an electrical lead 45 operably coupled to an electrode 46.

The processor 20 can be configured to reverse the pain signature in the brain of the patient 10 using neurostimulation (or more accurately, neuromodulation). For example, neuromodulation can include the application of electricity of a predefined voltage, frequency, current, and duration to the brain of a patient 10. Preferably, the neuromodulation applied to the brain of the patient 10 is configured to "jam" the neuronal activity of the patient 10 (i.e., rather than further stimulating it). Preferably, this neuromodulation is achieved by providing high frequency current (e.g., between 150-200 Hz, 1-3 volts, 1-3 mA, and substantially of 0.25-0.75 ms rectangular pulses of 1 second duration (assuming tissue impedance of 1000$\Omega$). Preferably, by delivering a low voltage, brief, and high frequency pulse to neuronal structures that preferentially respond to pain stimuli, the pain signature can transiently be reversed back to "normal." In addition, the neuromodulation protocol can be configured to transiently attenuate pain behavior in pain subjects to the level of that in naïve/normal, while otherwise retaining tactile sensitivity. Electrical treatment is provided to the deep brain, the VPL, and/or WDR neurons.

One exemplary treatment protocol includes electrical stimulation of the brain of the patient 10 using periodic pulses of electricity. For example, intermittent pulses (e.g., 1 pulse, every 1-3 hours) can be provided anywhere along the pain circuitry of the patient 10, but preferably in the brain VPL nucleus. Preferably, each of the pulses has a brief (e.g., 1 sec) duration, high frequency (e.g., 150-200 Hz), and a low voltage (e.g., 1.5-2 V). Preferably, each of these electrical pulses can "jam" the overactive circuitry in the brain of the patient 10, based on the temporal profile characterized herein. For example, for 2-3 hours, pain symptoms can be temporarily relieved after providing an electrical pulse.

The system 5 can be open-loop and/or closed-loop. In an open-loop embodiment, the system 5 can be programmed to provide electrical therapy according to a predetermined protocol (e.g., frequency, duration, voltage, amperage) without the use of the pattern recognition system 15 and the analog-to-digital converter 30. In an open loop-embodiment, the treatment protocol can be stored in a memory that is connected to the processor 20. In a closed-loop embodiment, the system 5 preferably uses information received via, for example, the pattern recognition system 15 and the analog-to-digital converter 30 to treat cognitive, affective, and emotive neurological conditions, owing to the characterization of the pain signature described herein. While the closed-loop system described herein discusses the use of an electrical lead 40 implanted in the brain of the patient 10, other configurations are possible (e.g., receiving diagnostic information from fMRI, or PET scanning). Additionally, while separate leads (e.g., leads 40, 45 are discussed, a single lead could instead be used for sensing and provision of the electrical signals. Additionally, the system 5 can be controlled manually (e.g., by actuating a button, or via a remote connection.

Figure 3:
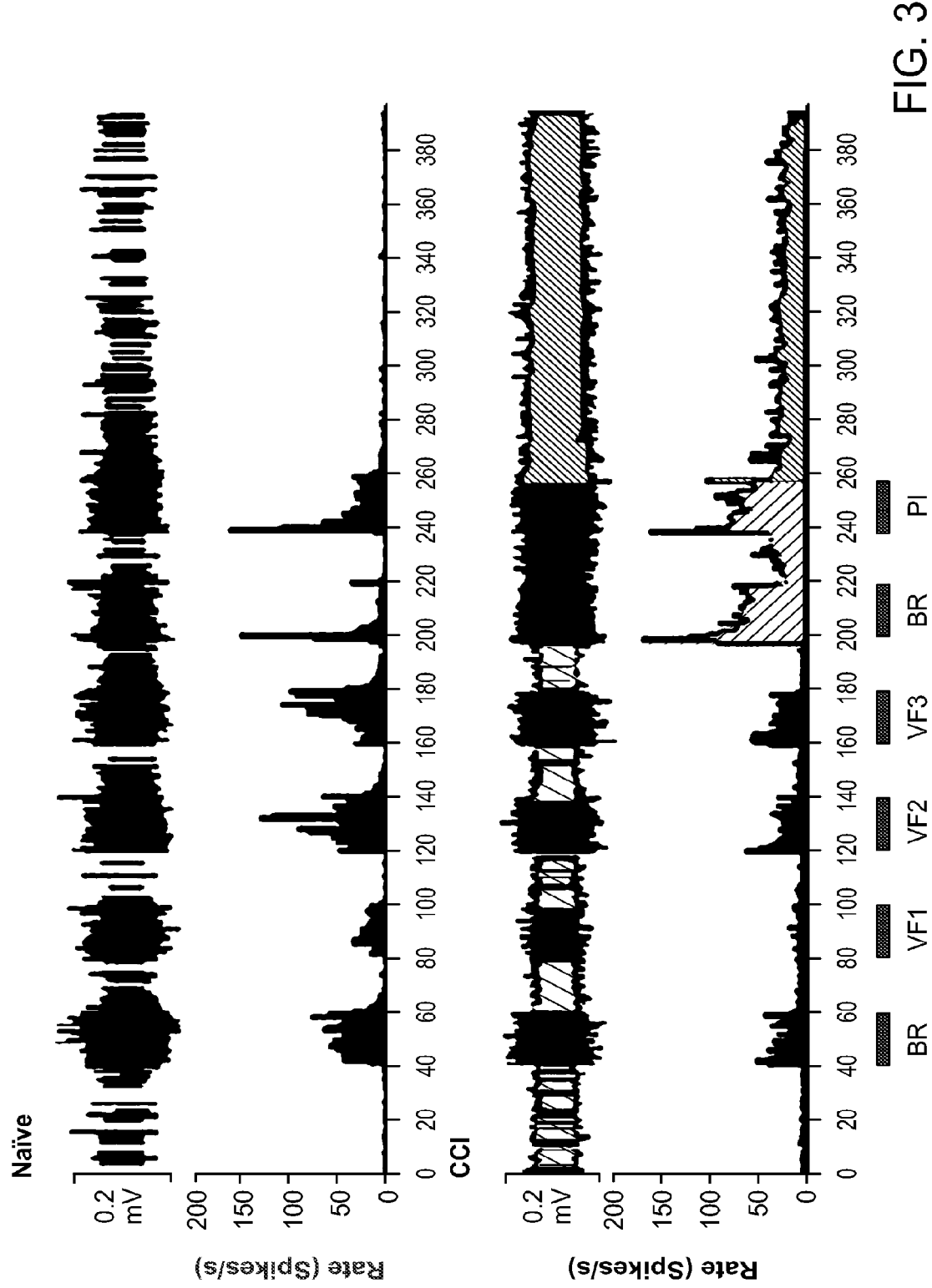
FIG. 3 is a graphical representation of a representative example of a single unit recording comparison between CCI and Naive subjects. Each graph displays the firing (mV) of a single WDR neuron over time and corresponding peristimulus time histograms of the data. Both VPL neurons used for recording possessed receptive fields at the hind-paw. CCI model rats display an increase in spontaneous background firing (shown in yellow), elevated pressure and pinch responses (green), and rhythmic after-discharge signaling (blue).
Figure 4:
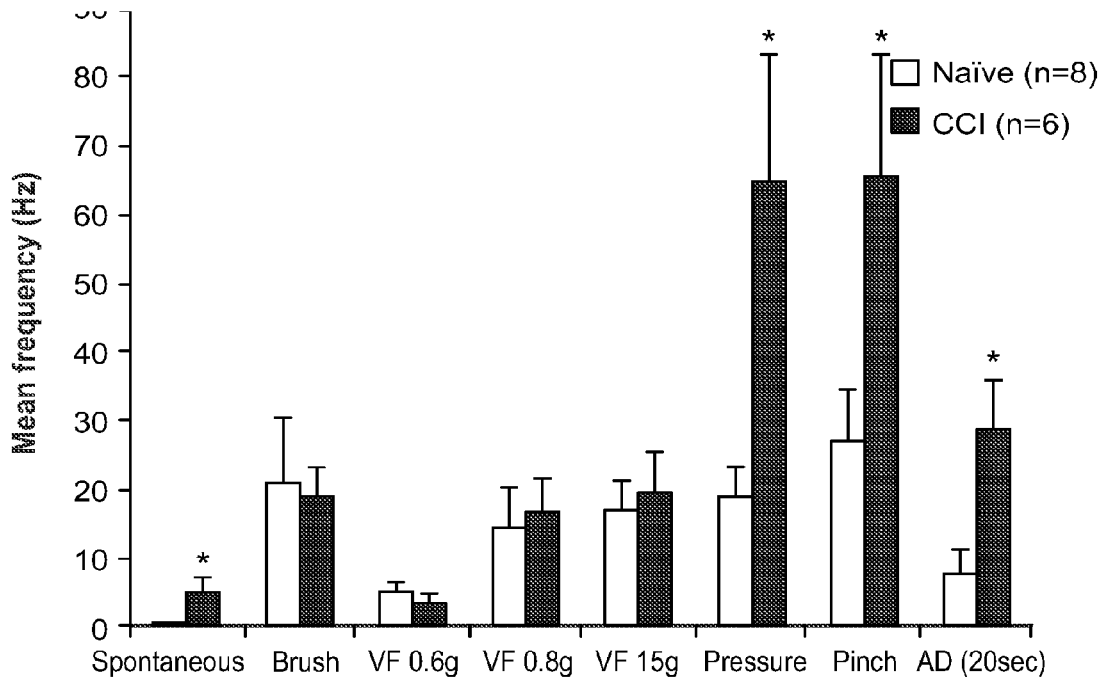
FIG. 4 is a bar graph showing a comparison of the mean evoked response frequency over all group 1 (CCI) and group 2 (naive) rats. Statistically significant increases in spontaneous activity and after discharge, as well as evoked pressure and pinch responses are shown (*$P<0.05$).
Figure 5:
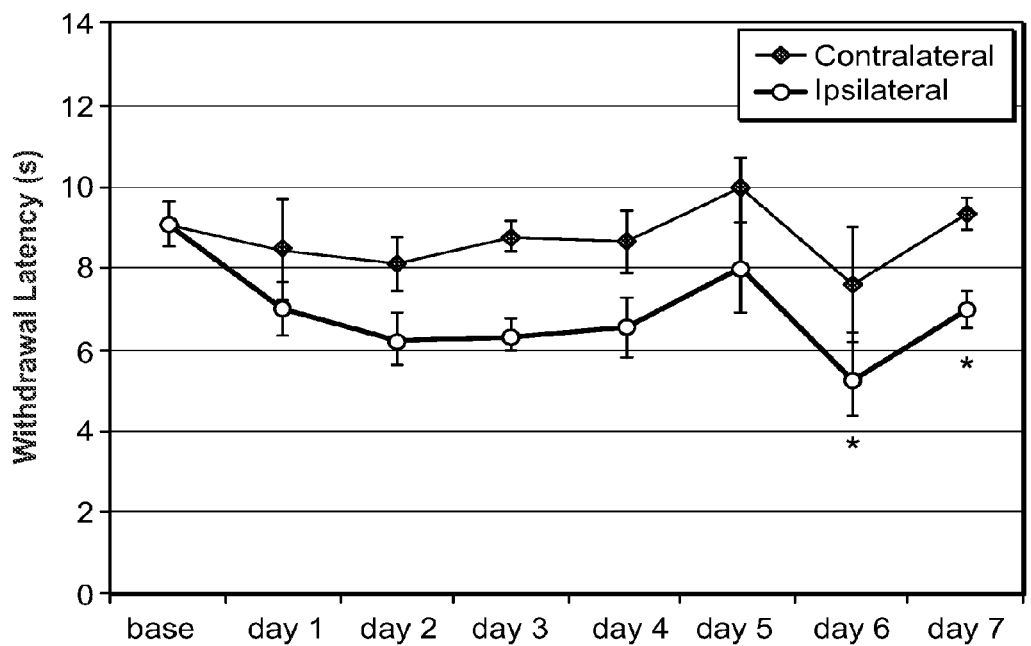
FIG. 5 is a line graph showing a comparison of rat withdrawal latency between the hindpaw ipsilateral and contralateral to the sciatic nerve injury as measured during behavioral testing. The withdrawal latency of the injured hindpaw (pink) is significantly lower than baseline by days 6 and 7 (* $P<0.0.5$).

Electrophysiological Measurements for Pain Signature:

Electrophysiological measurements of wide dynamic range (WDR) thalamic neurons in chronic constriction injury (CCI) rats indicate elevated evoked response to pressure and pinch stimuli in addition to rhythmic afterdischarge signaling and an increase in spontaneous background firing (FIGS. 3 and 4), in addition to abnormal burst. The group of rats that underwent CCI followed by thermal behavioral testing (n=10) display a statistically significant (P<0.05) decrease of the ipsilateral hindpaw withdrawal reflex over the course of one week, with a marked separation in the withdrawal latency of the ipsilateral and contralateral hindpaws (FIG. 5). Treatment efficacy was assessed in part based on the reversal of this known effect.

Figure 6:
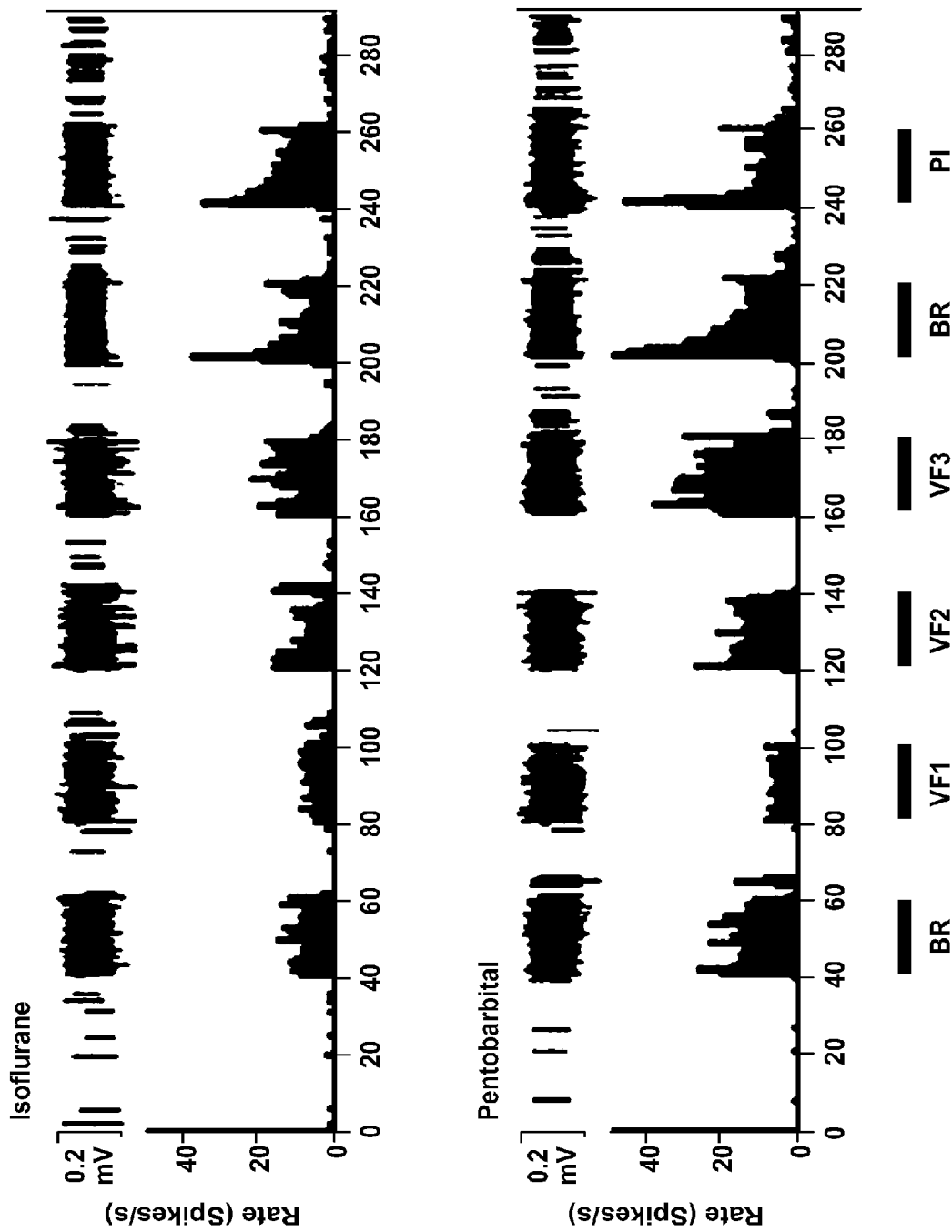
FIG. 6 is a graph showing a representative example of a comparison between Isoflurane and Pentobarbital anesthesia. Activity in a single VPL unit is recorded under conditions of Isoflurane (2%) followed by Pentobarbital 20 minutes later (i.v. 40 mg/kg/hr) in a single animal. No major difference in spontaneous or evoked activity is apparent.

Anesthesia:

No significant difference resulted in neuronal activity under intravenously administered pentobarbital sodium as compared with isoflurane gas anesthesia (FIG. 6). For this reason, animals were tested exclusively with isoflurane gas and generalizations may be applied across experiments with a variety of anesthetization methods.

Figure 7:
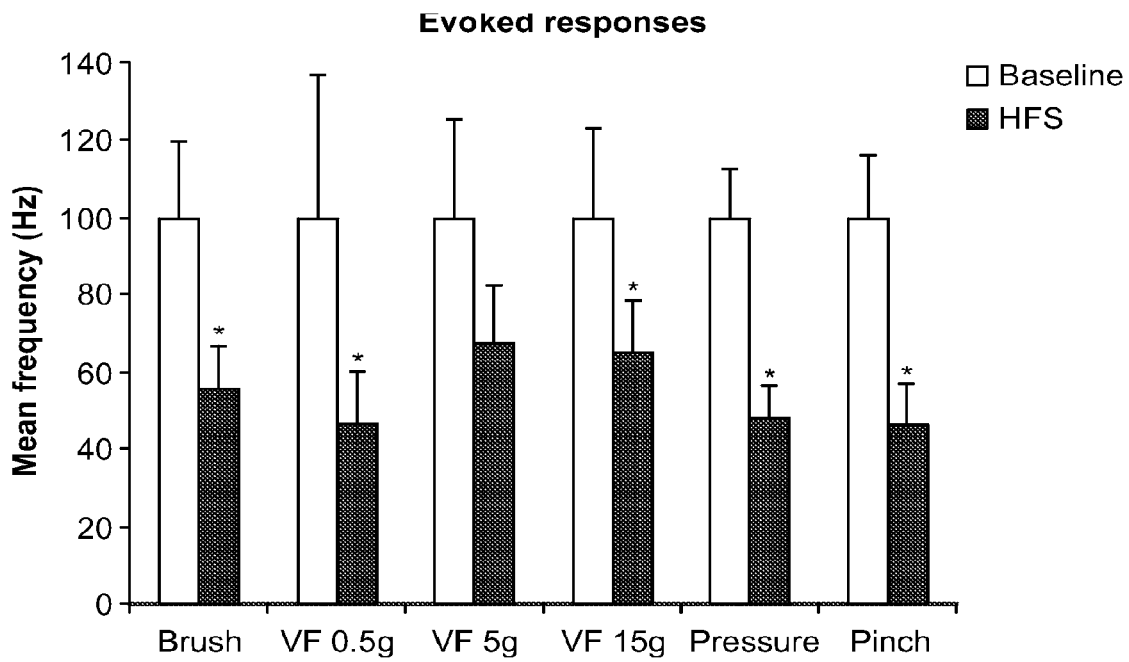
FIG. 7 is a bar graph showing an electrophysiological response to mechanical stimuli in pre- and post-HFS conditions. VPL neurons of group 5 rats post HFS are significantly less reactive to mechanical stimuli via brush, Von Frey, pressure, and pinch than during initial baseline recording ($P<0.05$).
Figure 8:
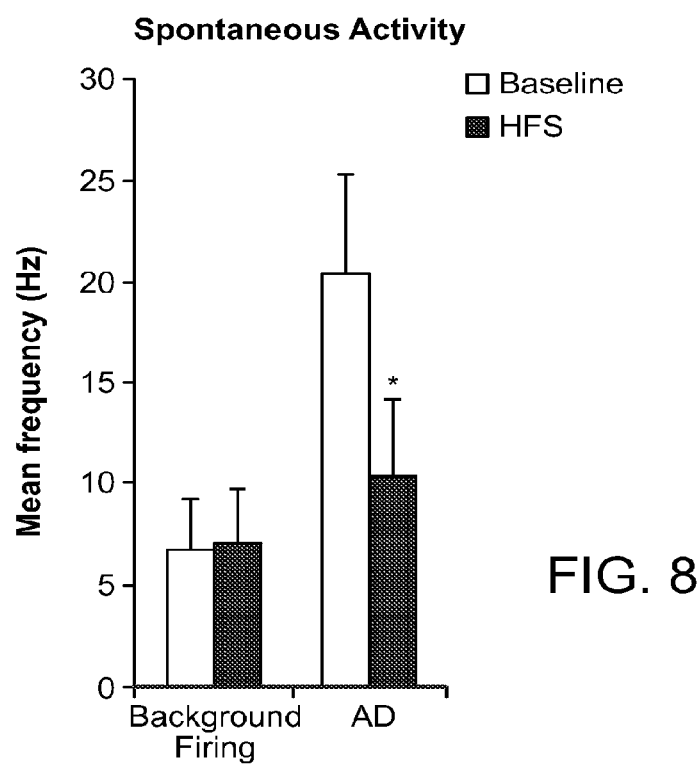
FIG. 8 is a bar graph showing a background electrophysiological comparison in pre- and post-HFS conditions. VPL neurons of group 5 rats post HFS display significantly lower levels of afterdischarge (20 seconds post mechanical stimulation) while levels of background firing remain relatively constant (* $P<0.05$).
Figure 9:
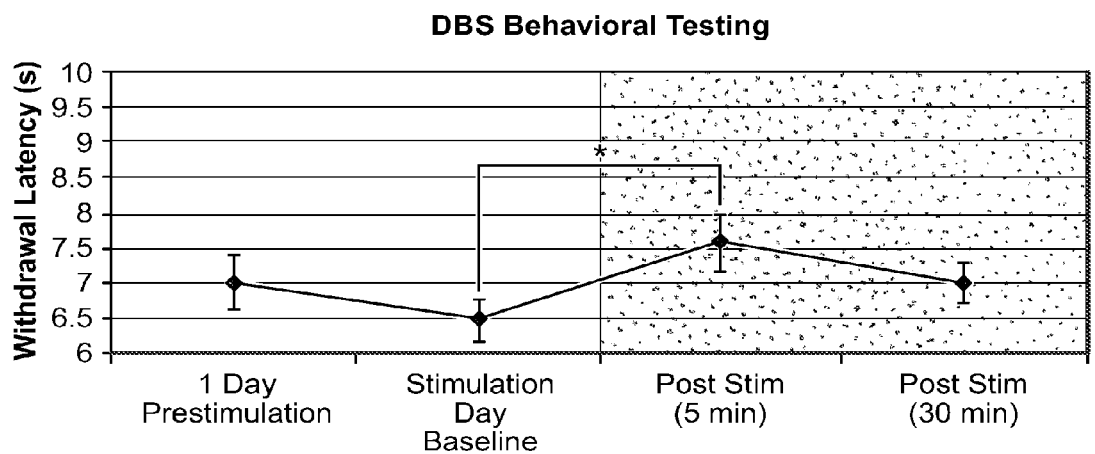
FIG. 9 is a line graph showing withdrawal Latency of the ipsilateral hindpaw in deep brain stimulation (DBS) group 6 rats. Within 5 minutes of neurostimulation, withdrawal latency significantly increases, with effects lasting 0.5-2 hrs.

Deep Brain Stimulation:

Deep Brain Stimulation of CCI animals resulted in an attenuation of mean firing rate in response to all forms of mechanical stimuli, in addition to a statistically significant decrease in afterdischarge (FIGS. 7 and 8). Furthermore, behavioral testing of awake DBS rats in group 6 revealed a corresponding increase in withdrawal latency following high frequency DBS (FIG. 9; data represent values normalized to pre-FHS or Baseline 100%).

Figure 10:
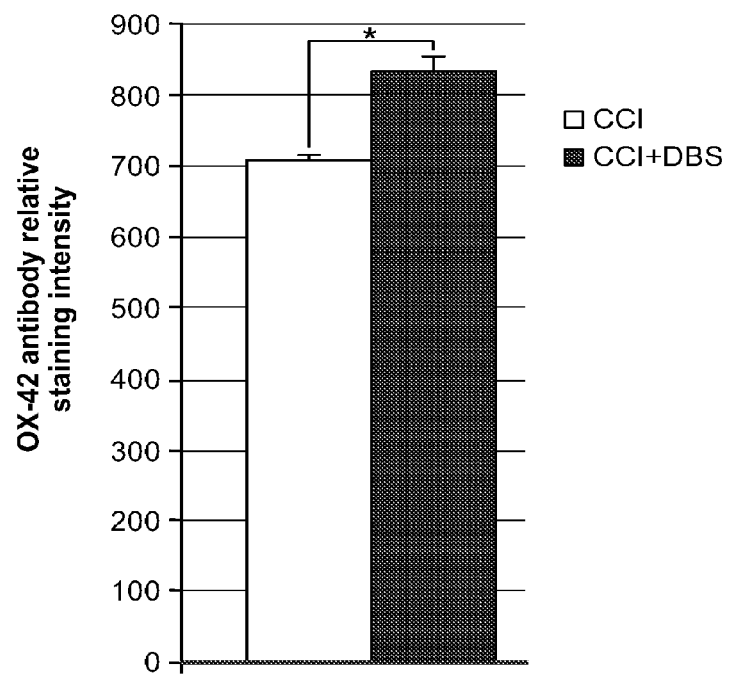
FIG. 10 is a bar graph showing OX-42 antibody staining comparison between CCI and CCI+DBS animals in VPL contralateral to CCI (i.e. receiving pain input from the injured leg and the implant), DBS subjects displayed significantly higher levels of OX-42 antibody staining as compared with untreated CCI subjects (*$P<0.05$). Reflected differences were measured as changes in the mean grayscale value of photographed microscope images of the VPL, indicating a physiologic local effect for HFS.
Figure 11:
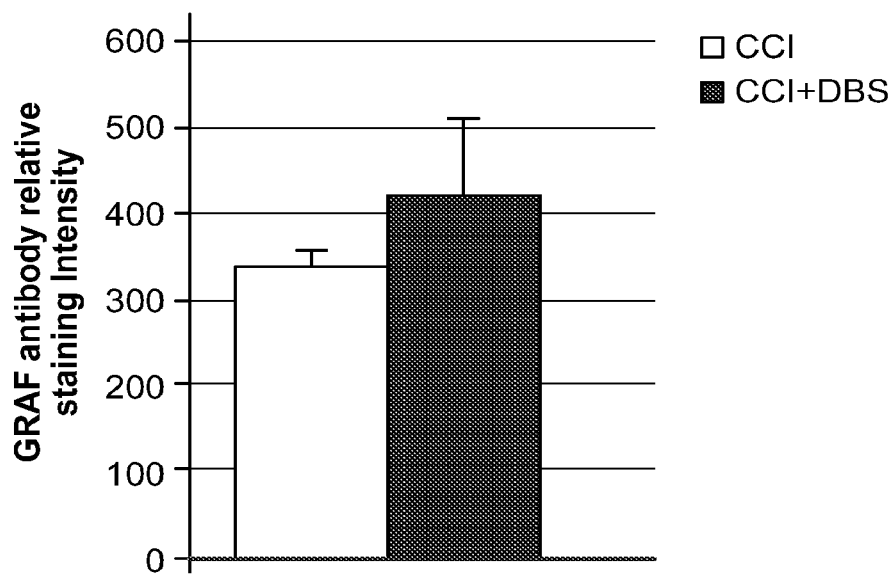
FIG. 11 is a bar graph GFAP antibody staining comparison between CCI and CCI+DBS animals in VPL contralateral to CCI (i.e. receiving pain input from the injured leg and the implant). Measured differences in GFAP staining were not statistically significant, suggesting lack of astrogliosis, tissue scarring or prominent neuroinflammatory reaction to HFS.

Histology:

Postmortem histological analysis of these rats as compared with CCI control animals is indicative of a statistically significant bilateral increase in VPL Ox 42 antibody staining (P<0.05) while levels of GFAP antibody staining remain constant (FIGS. 10 and 11).

Figure 12:
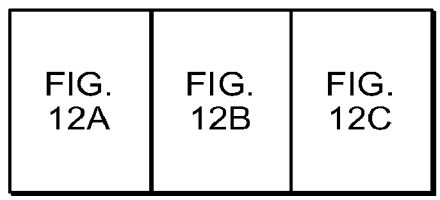
FIG. 12A-C are a series of bar graph showing burst characterization in response to various stimuli, e.g., brush, Von Frey, pressure, and pinch.
Figure 12A:
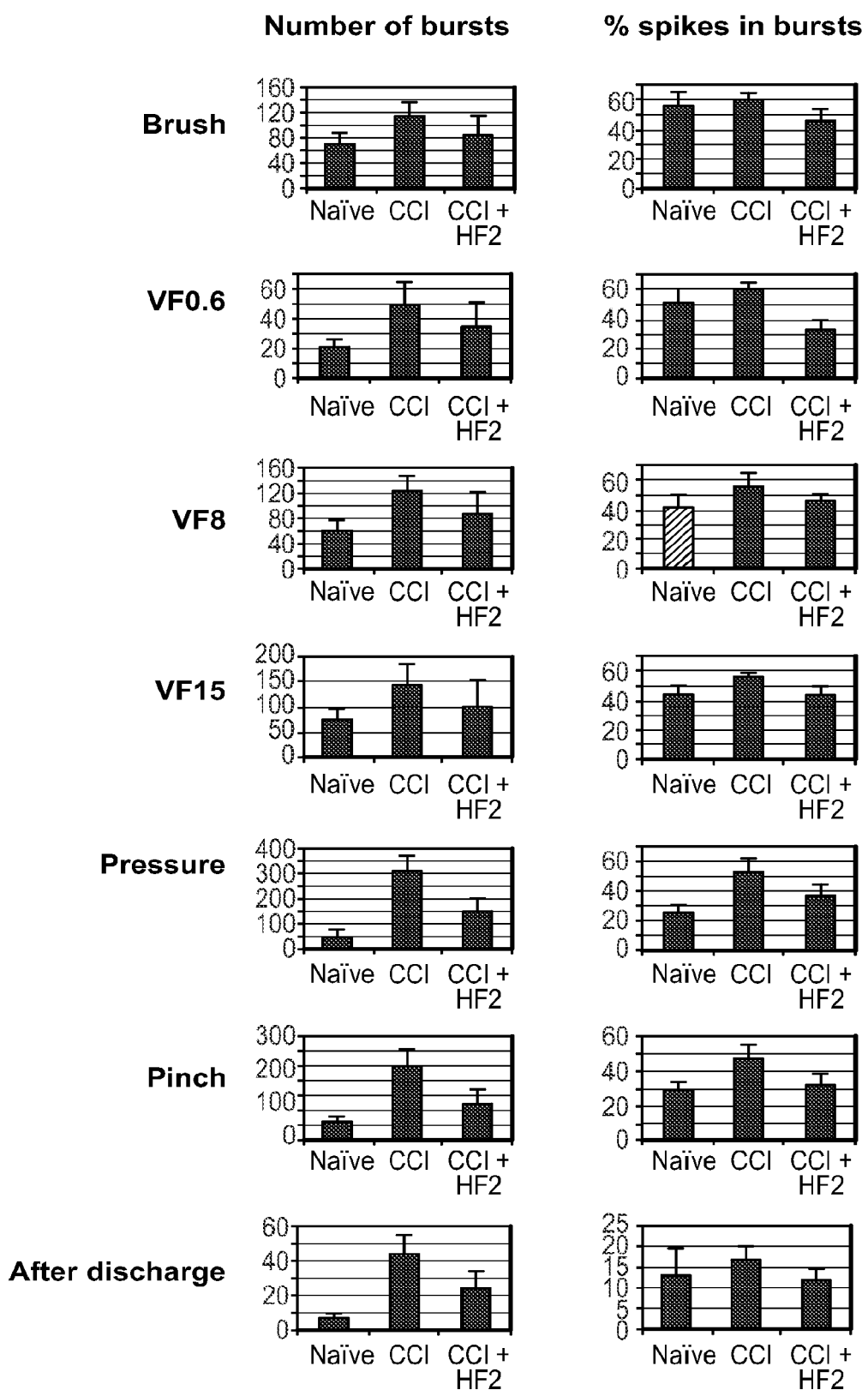
Figure 12C:
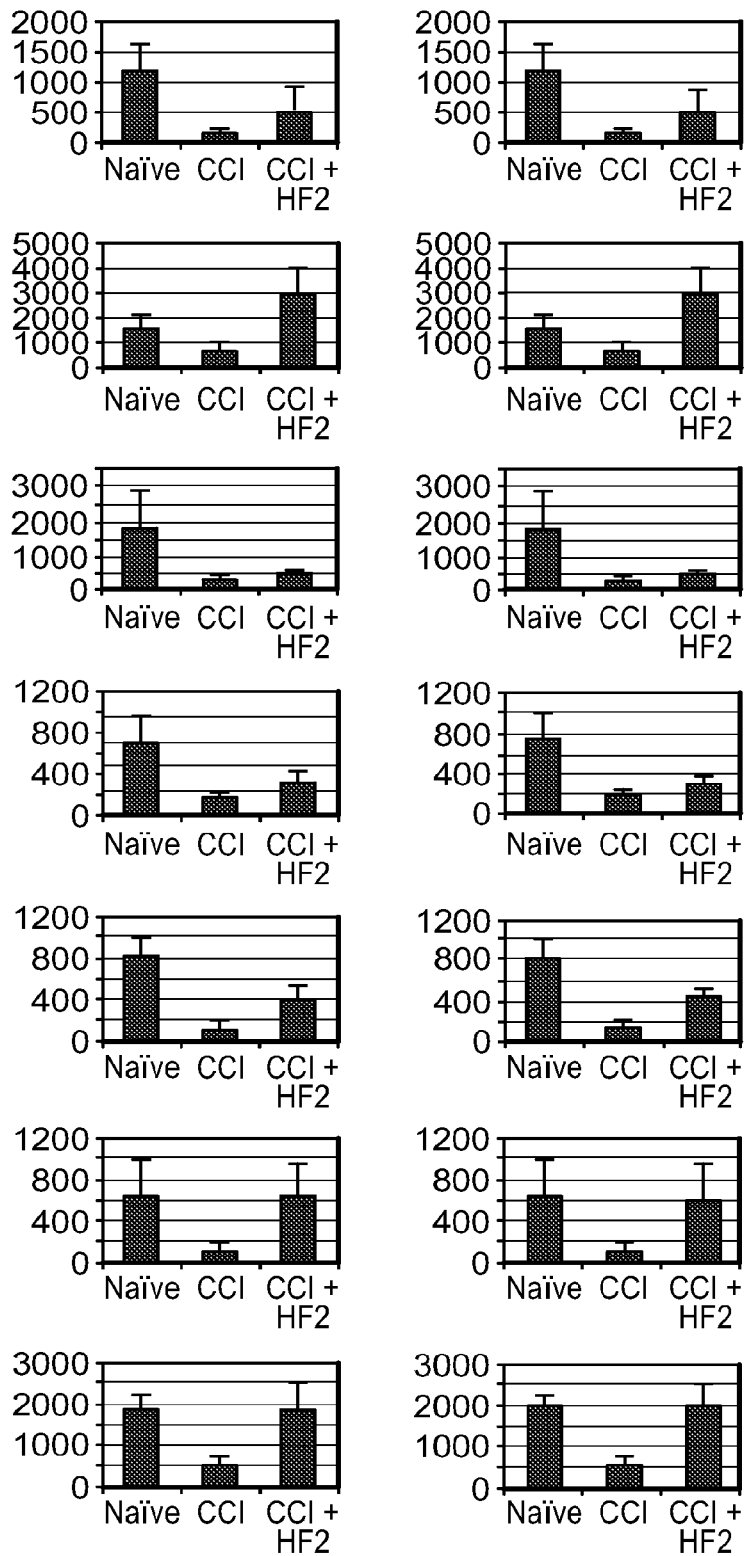

FIG. 12 shows characterization of bursts in response to various stimuli. The Requirements for defining bursts were:
Maximum interval signifying burst onset (6 ms)
Maximum interspike interval (9 ms)
Longest increase in interspike interval within a burst (2 ms)
Minimum number of spikes within a burst (2).

The following methods were used to generate the data described herein.

CCI: Chronic Constrictive Injury (CCI) was induced 7-9 days prior to data acquisition. Animals were anesthetized with isoflurane (2.5%). The surgical procedure consisted of a modification of the original loose ligation model designed by Bennett and Xie. The process involved isolation of the sciatic nerve via blunt dissection of the biceps femoris followed by a unilateral loose ligation with 5-0 gauge chromic gut ligature at three sites above the branching of the nerve, 1 mm apart. The ligation initiates an inflammatory response that results in chromic gut constriction of the nerve. Following the surgery, overlying muscles and skin were closed with 4-0 nylon sutures and the rodents were allowed time for recovery. Thermal hyperalgesia resulting from CCI has been found to remain relatively constant for a period of 5-27 days following the injury.

Electrophysiology: Single unit firing-unit recording (i.e. sampling neuronal activity one at a time) was recorded under deep anesthesia (1.5% Isoflurane). Extracellular single-unit recordings in and were made with a 0.005" 5M $\Omega$ Teflon-coated silver microelectrode (A-M Systems, Carlsborg, Wash.). DBS animals were implanted with a modified electrode as shown below (FIGS. 14, 15, 16). Each subject was placed in a stereotaxic frame, and a limited craniotomy exposed the brain surface vertical to the recording sites within the VPL [Bregma (−3.3; −2.5); lateral (2.8; 3.6); vertical (5.4; 6.4)] (FIG. 16). Electrical signals were amplified and filtered at 3000 Hz and processed with a CED micro 1401 data acquisition system and SPIKE-2 software (Cambridge Electronic Design, Cambridge, England).

Waveforms were sorted to extract activity of a single neuron using automated template-matching. A hydraulic micropositioning device (Kopf Instruments, Tajunga, Calif.) was employed in all vertical electrode penetrations through nervous tissue. As the microelectrode is lowered into the estimated region, a single "unit" or neuron can be isolated by stimulating the suspected somatosensory receptive field via tapping, brushing, pinching the skin, or manipulating the limbs of the anesthetized subject until excitation at the location of the electrode tip is measured via changes in current. This process was used in order to identify VPL units innervated by the sciatic nerve. Spontaneous activity was then measured, followed by evoked responses to mechanical stimulation within the receptive field. Six mechanical stimuli were applied during each recording session: (i) brush (BR); (ii-iv) increasing intensity von Frey filaments (0.6 g, 8 g, and 15 g forces); (v) pressure (PR); (vi) pinch (PI). Wide Dynamic Range (WDR) thalamic neurons were specifically targeted based on their response to each of the mechanical stimuli.

Alternative Anesthesia Preparation: During preliminary trials, an additional cohort of animals underwent either tracheal intubation for the administration of 1.2%-2% isoflurane, or IV cannulation for the administration of pentobarbital sodium (40 mg/kg/hr) prior to electrophysiological recording. The purpose of these groups was to establish the minimal effect of anesthesia type and level on VPL firing activity.

DBS: After measurements of at least 2 consecutive series of recording spontaneous and evoked activities, the electrode was disconnected from the recording equipment. The cathode of an isolated pulse stimulator was connected to the electrode and the anode was connected to the skin of the rat at the base of the head, acting as a body ground. Preliminary rectangular pulses 0.5 ms in width were applied at a frequency of 100 Hz at 0.5V for 1 s. Immediately after stimulation, the electrode was disconnected from the stimulator and reconnected to the recording equipment and recording resumed. Background activity was recorded for 40 s and progressive mechanical stimuli as described above were then applied for a duration of 20 s each with 40 s rest in between each. For any given unit, when there was no apparent change in activity, electrical stimulation was applied again with an increase in intensity (to 1.0 V or 1.5 V), frequency (from 100 Hz to 200 Hz), or number (5 times every 3 s) of stimuli. The maximum stimulation was 1.5V at 200 Hz for is repeated every 3 s for a total of 5 pulse events. When there was an apparent inhibition of the responses to at least one mechanical stimulus, DBS was stopped and consecutive electrophysiological recordings of a series of spontaneous and evoked activities were tested every 10 min.

Behavioral Testing: Behavioral tests of the CCI rats were performed with respect to thermal and mechanical stimulation in order to verify the presence of allodynia and hyperalgesia. Each animal was placed in a Plexiglas chamber situated on an elevated glass plate 30 minutes prior to testing for acclimatization. The thermal behavioral test consists of focusing a radiant heat source (4.7 amps) through the glass floor onto the plantar surface of the rat's hind limb, resulting in withdrawal behavior. The measured withdrawal latency is defined to begin at the onset of laser beam exposure and end upon movement of the rat hind paw from the floor surface. Five stimulation pulse events separated by 5 min were averaged for each hindpaw and reported as the withdrawal latency for a given session. In order to test the effectiveness of HFS therapy on awake rodents, one group of animals underwent behavioral testing throughout the DBS treatment regimen. DBS electrodes were held in place with orthodontic resin and microelectrode leads were stored in a small plastic container surgically implanted at the base of the skull during behavioral trials. All DBS behavioral testing animals received initial stimulation at 1.5V and 200 Hz within 6-8 days post surgery. Baseline pre-operative behavioral data was recorded for analysis beginning one day prior to initial neurostimulation. Following the DBS event, behavioral tests were repeated 5 minutes and 30 minutes post treatment.

Histology and Image Analysis: In addition to verifying electrode placement, supplementary postmortem tissue analysis was used to identify the activation levels of glial cells in the region of interest. This provided the opportunity to assess microgliosis and astrogliosis associated with glial scarring. In order to obtain images for subsequent analysis, animals are anesthetized (5% isoflurane) and transcardially perfused with ice cold phosphate buffered saline (PBS) supplemented with 10 USP units of anticoagulant Heparin Sulfate for 5 minutes (10 ml/min) followed by cooled 4% paraformaldehyde (PFA) in PBS for 5 minutes (10 ml/min). This fixation process was used in order to preserve nervous tissue form degradation. Following decapitation with a small animal guillotine, the head was stored in PFA over night. The brains were then removed and stored in cold 30% sucrose until fully impregnated. The formalin-fixed brains were blocked in the desired orientation and placed in tissue-embedding media (O.C.T. Compound 4583, Tissue-Tek). Brains were stored at −80 degrees Fahrenheit and cut into 30 μm sections with a microtome. These sections (ranging from Bregma −2.12 mm to −4.16 mm) were mounted on slides, dried, and stained with OX-42 or GFAP for further analysis of microglia or actrocytes, respectively. All histological images were captured via fluorescent microscope (Eclipse 80i, Nikon with X-cite 120 EXFO fluorescent illumination). Photographs were taken via a high sensitivity digital camera (Retiga Exi Fast 1394, Q Imaging), and were then uploaded and digitally analyzed using IP LAB software (version 3.94r4, Scanalytics Inc). For quantitative comparison, the mean grayscale value of a 500×500 pixel region of interest for each image was used as an approximate measure of cell density.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Example 1

Single-Unit Physiology in the Ventral Posterolateral Nucleus of the Thalamus in Neuropathic Rats Neuropathic pain secondary to nerve injury is often chronic and accompanied by dysesthesias. It is linked to long-term changes in neuronal physiology, known as neuroplasticity, which is well described in peripheral nerves and the spinal cord but relatively less understood in the brain. In spite of recent advances in pharmacotherapy, neuropathic pain remains poorly managed.

An early clinical account of aberrant thalamic physiology was documented, which was later localized to the intralaminar, medial and ventral thalamic nuclear groups of patients with neurogenic pain, central deafferentation pain, as well as peripheral neuropathic pain. Under these painful conditions, single unit activity is generally described in terms of higher probability of spontaneous firing, increased rate of evoked firing, ectopic bursting, and dysrhythmic activity.

Clinical evidence of aberrantly firing thalamic neurons in chronic pain is corroborated by data from animal models. In rats with central pain following spinal cord injury, neurons in the ventral posterolateral (VPL) nucleus of the thalamus manifest higher probability of spontaneous firing, afterdischarge, increased evoked responses and characteristic bursting patterns. In comparison, little is known about changes in tonic or burst firing of VPL neurons following peripheral neuropathic injury without central lesion.

Nociceptive neurons in the VPL receive ascending projections mainly from spinothalamic tract neurons and project to several cortical areas including the primary somatosensory cortex. Within the VPL, a group of neurons responds to a wide dynamic range (WDR) of mechanical stimuli, phenotypically homologous to WDR neurons at spinal cord level whose role in central sensitization and chronic pain is well documented.

In addition to the correlation between pain and neuroplasticity, the therapeutic effects of neuromodulation by deep brain stimulation (DBS) further suggests that brain plasticity is likely to have functional significance. For example, DBS in the periaqueductal gray and motor cortex effectively relieves pain symptoms and decreases the requirement for pain medication. More than 1000 clinical cases of DBS for chronic pain were preformed in the seventies and eighties. Although the Food and Drug Administration (FDA) rescinded its approval in the late eighties, there has been resurgence of interest in this medical procedure in the last decade with an emphasis on patient selectivity and, more importantly, understanding basic mechanisms. Regarding DBS in the VPL, information related to the effects of microstimulation on neuroplasticity and sensory phenomena is limited, with clinical studies reporting mixed results.

Although the mechanisms of DBS are not well understood, stimulation frequency represents a key factor, with high frequency stimulation (HFS, >100 Hz) mimicking the functional effects of ablation, also referred to as 'jamming' of local circuitry. HFS in the VPL reduces mechanical allodynia in rats with peripheral neuropathy.

HFS can be used to inhibit hyperactive VPL neurons, thus reversing neuroplasticity and, consequently, behavioral hypersensitivity. The firing of single units extracellularly from VPL neurons in naïve rats was recorded. Firing from neuropathic rats after chronic constriction injury (CCI) of the sciatic nerve was also recorded. The data show that tonic and burst firing patterns in rats with CCI were significantly different from those in naïve rats and were partially reversed after micro stimulation in the VPL at high (but not low) frequency, with subsequent attenuation of hyperalgesia.

The following materials and methods were used to generate the data described in this example.

Adult Male Sprague-Dawley rats (250-300 g) were used in this study.

Chronic constriction injury (CCI). As previously described (Owolabi S A, Saab C Y (2006) Fractalkine and minocycline alter neuronal activity in the spinal cord dorsal horn. FEBS Lett 580:4306-4310; LeBlanc B W, Iwata M, Mallon A P, Rupasinghe C N, Goebel D J, Marshall J, Spaller M R, Saab C Y (2010) A cyclic peptide targeted against PSD-95 blocks central sensitization and attenuates thermal hyperalgesia. Neuroscience 167:490-500; both of which are hereby incorporated by reference), a modified CCI from the originally described model (Bennett G J, Xie Y K (1988) A peripheral mononeuropathy in rat that produces disorders of pain sensation like those seen in man. Pain 33:87-107; hereby incorporated by reference) was performed. The sciatic nerve was exposed after skin incision at the mid-thigh level and blunt dissection of the biceps femoris under deep anesthesia (isoflurane 3-4%). Three chromic gut (5-0) ligatures were tied loosely around the nerve 1 mm apart, proximal to its trifurcation. After CCI, the overlying muscles and skin were closed in layers with 4-0 nylon sutures and the animal was allowed to recover. Rats were then maintained under the same pre-operative conditions and fed ad libitum. At day 7 after CCI, neuropathic manifestations are persistent for several weeks thereafter.

Single-unit extracellular recording. Animals from naïve and CCI groups underwent extracellular single unit recording from VPL neurons according to established methods (Haim B C, Saab C Y, Waxman S G (2006) Alterations in burst firing of thalamic VPL neurons and reversal by Na(v) 1.3 antisense after spinal cord injury. J Neurophysiol 95:3343-3352; hereby incorporated by reference). The activity of 1-2 units/animal was recorded. Rats were initially anaesthetized with isoflurane (4% in induction chamber), and maintained by tracheal intubation (1.5%; interestingly, no difference was noted in the firing rate under isoflurane or pentobarbital sodium (60 mg/kg) anesthesia). The head was fixed in a stereotaxic apparatus (Kopf Instruments, Tujunga, Calif., USA) and skin incision and a limited craniotomy exposed the brain surface vertical to the recording sites within the thalamus. Neuronal units were isolated from the VPL nuclei of the thalamus [respective stereotaxic coordinates in mm: bregma (−3.3, −2.5); lateral (2.8, 3.6); vertical (5.4, 6.4)]. Extracellular single-unit recordings were made with a 5 MΩ Teflon-coated tungsten microelectrode (A-M Systems, Carlsborg, Wash., USA). Electrical signals were amplified and filtered at 300-3000 Hz (DAM80, World Precision Instruments, Sarasota, Fla., USA), processed by a data collection system (CED micro1401mkII; Cambridge Instruments, Cambridge, UK) to construct peristimulus time histograms. The stored digital record of individual unit activity was retrieved and analysed off-line with Spike2 software (Cambridge Electronic Design, CED, Cambridge, UK). Once a unit was identified by a gentle probing of the body surface, its receptive field was mapped and stimulated by an experimenter.

For testing evoked activity, six routine natural mechanical stimuli were applied in the following order: brush, by a cotton applicator to the skin; three von Frey filaments (0.6, 8 and 15 g) with enough force to cause buckling of the filament at a regular frequency of 1 application per sec; pressure, by attaching a large arterial clip with a weak grip to a fold of skin (144 g/mm$^2$) and pinch, by applying a small arterial clip with a strong grip to a fold of skin (583 g/mm$^2$). Multireceptive units were identified by their responsiveness to brush, pressure and pinch, and with increasing responsiveness to incrementing strength von Frey stimuli. Care was taken to ensure that each stimulus was applied to the primary receptive field, and that isolated units displayed action potentials that remained stable for the duration of each experiment using Spike2 template matching. Firing activity was computed as mean frequency of spikes/20 s, and evoked responses and after discharges were calculated by subtracting the pre-stimulus baseline activity to yield a net increase in discharge rate. Afterdischarge was defined as continuous discharge after noxious pinch stimulus removal for 20 s. Cursors were set at the beginning and the end of the stimulus, and all of the spikes occurring between the cursors were summed. Cursors were also set at the beginning of the trace and after 40 s (baseline or un-evoked firing), and the spikes occurring during this period were summed to provide a measure of the background activity. The two sums were divided by the respective duration and the resulting averages (spikes/s) subtracted to yield the value attributed to the response (total number of spikes/s in excess of the background activity during the stimulus). One to two neurons with individually mapped receptive field were recorded from each rat. Neuronal activity was analyzed off-line using Spike2.

In some rats, the spinal cord was also exposed by laminectomy at thoracic (T4-T6) level and topical 2% lidocaine was applied using a cotton pledget to the dorsal and lateral surfaces of the spinal cord, followed 10 min later by complete cord transection using fine scissor while recording from the VPL neuron continued.

Estimated charge density. A theoretical limit of 30 µC/cm2 has been proposed for the maximal allowable charge density above which tissue damage occurs (Medtronic (1998) DBS TM technical manual. Minneapolis: Medtronic; Kuncel A M, Grill W M (2004) Selection of stimulus parameters for deep brain stimulation. Clin Neurophysiol 115:2431-2441; Shimojima Y, Morita H, Nishikawa N, Kodaira M, Hashimoto T, Ikeda S (2010) The safety of transcranial magnetic stimulation with deep brain stimulation instruments. Parkinsonism Relat Disord 16:127-131; each of which is hereby incorporated by reference), based on the following formula:

$$\frac{\text{Voltage (V)} \times \text{Pulse width (µs)}}{\text{Impedance (Ω)} \times \text{electrode SA (cm}^2\text{)}}$$

Accordingly, given the following approximations of stimulation parameters at 1 V, 500 is width, 1500Ω and 0.02 cm$^2$ electrode tip surface area, the charge density within the vicinity of the silver microelectrode tip used in our behavioral experiments is roughly 16 µC/cm$^2$, i.e. below maximal density (charge density for Tungsten microelectrodes used in the acute electrophysiology experiments is much lower due to higher electrode impedance). In addition, modeling studies suggest the possibility of 'current steering' using bipolar stimulating electrodes so that the shape of the area subjected to stimulation can more closely overlap with a particular region of interest in the brain, therefore improving stimulation efficacy and minimizing side effects. Referring to modeling studies (e.g., Butson C R, Maks C B, McIntyre C C (2006) Sources and effects of electrode impedance during deep brain stimulation. Clin Neurophysiol 117:447-454; Butson C R, McIntyre C C (2006) Role of electrode design on the volume of tissue activated during deep brain stimulation. J Neural Eng 3:1-8; Butson C R, McIntyre C C (2008) Current steering to control the volume of tissue activated during deep brain stimulation. Brain Stimul 1:7-15), the stimulation parameters with a monopolar electrode would theoretically result in a spherical electric field with a radius of approximately 2 mm, whereas considering the bipolar electrode design and their orientation in the brain, an optimal overlap was predicted between the electric field potential and the VPL nucleus according approximations illustrated in FIG. 17.

Burst analysis. Burst events were identified using Spike 2 Burst script using the following criteria: 6 ms of the maximum interval between two events that signifies the start of a burst, 9 ms of the longest interval between two events within a burst, and 2 of the minimum number of events in a burst. The following parameters were calculated during the recording periods of background activity, six natural mechanical stimuli evoked discharges and after discharge: Number of burst events, mean inter burst time (ms), and % spikes in burst:

Mean spikes/burst×Number of bursts×100

Total Spikes

Micro-stimulation in the VPL. To test the effect of microstimulation on neuronal firing in anesthetized rats, the same recording electrode was used for microstimulation within the VPL. After identifying single units and recording pre-stimulation (baseline) firing rates, the electrode was disconnected from the recording equipment and connected to a stimulator (A-M Systems Isolated Pulse Stimulator). Rectangular pulses 0.5 ms width were applied at a frequency of 100 Hz at 0.5 V for 1 s. Immediately after stimulation, the electrode was disconnected from the stimulator and reconnected to the recording equipment and data acquisition resumed within 2-3 min after baseline measurements. For any given unit, if no change in firing was apparent after stimulation, electrical stimulation was applied again with an increase in intensity (1.0 V and 1.5 V), frequency (100 Hz and 200 Hz), respectively, up to 5 microstimulation pulses every 3 s. When at least one evoked response was modulated by microstimulation, DBS was stopped and consecutive electrophysiological recordings of firing rates were tested every 10 min. Therefore, for any given unit, "minimum" stimulation consisted of a single 0.5 V, is pulse at 100 Hz, and "maximum" stimulation consisted of 5×1.5 V, 1 s rectangular pulse at 200 Hz.

To test the effect of microstimulation on behavior in non-anesthetized rats, bipolar silver wires (~1.5 KΩ) were chronically implanted on the day of CCI. Electrode segments were fused together with Epoxy resin forming cathode and anode. Teflon coating was removed exposing 0.5 mm on each electrode tip, which were separated by 1 mm from tip-to-tip vertically. Initially, the longer tip was connected to the recording equipment and local field potentials were recorded to localize the VPL area with a receptive field in the contralateral hindpaw (see description below for additional details on the orientation of the electrodes relative to the VPL for optimal steering of electric field and overlap with VPL nuclear structure). When a distinct increase in activity was recorded in response to mechanical probing of the hindpaw, the wires were fixed to the skull permanently using a screw and orthodontic resin while microelectrode leads were encased in a small plastic container fixed to the base of the skull. Withdrawal latencies were measured 5 min before (baseline) and up to 2 hr after micro stimulation (3×1.5 V, 1 s rectangular pulse at 200 Hz; A-M Systems Isolated Pulse Stimulator).

Behavioral analysis. Thermal sensitivity of the paw was assessed by measuring the latency of the withdrawal reflex in response to a radiant heat source. Animals were placed in Plexiglas boxes on an elevated glass plate under which a radiant heat source (4.7 amps) was applied to the plantar surface of the hindpaw. Paw withdrawal latencies (PWLs) of five stimulations, separated by 5 min rest, were averaged for each paw. For 'baseline' pre-operative values, data were averaged for both paws as no difference was observed in PWLs between paws.

OX-42 and GFAP immunoreactivity. Rats were anesthetized with pentobarbital (60 mg/kg, i.p.) then perfused intracardially with ice-cold PBS followed by buffered 4% paraformaldehyde. Brains were post-fixed with buffered 4% paraformaldehyde overnight, equilibrated in 30% sucrose, and frozen to −80° C. in OCT cryogenic compound (TissueTek Sakura). Coronal sections (30 μm) were adhered to glass slides and blocked with goat serum. Sections were stained for OX-42 (Santa Cruz Biotech, mouse IgG, 1:50), or GFAP (Chemicon International, mouse IgG, 1:100) overnight at 4° C. Slides were washed with PBS and probed with goat anti-mouse IgG (VectorLab 1:2000), visualized with a Nikon Eclipse Fluorescent microscope, and images were captured using a Qiacam CCD camera. Mean fluorescent intensity was measured using ImageJ (NIH v1.43n) in 3 predetermined non-redundant (160 μm)2 boxes within the VPL bilateral to CCI per slide in each animal.

Statistical analysis. All statistical tests were performed at the alpha level of significance of 0.05 using parametric tests. Data were tested for significance using one-way ANOVA to determine degree of variability within a sample and whether there was a difference between groups among the obtained means. Tests of factors including pairwise comparisons were carried out where appropriate, with either the paired Student's t-test for before-after comparisons or the two sample Student's t-test to compare two groups. Data management and statistical analyses were performed using Excel and presented as mean±standard deviation.

Figures 18A, 18B:
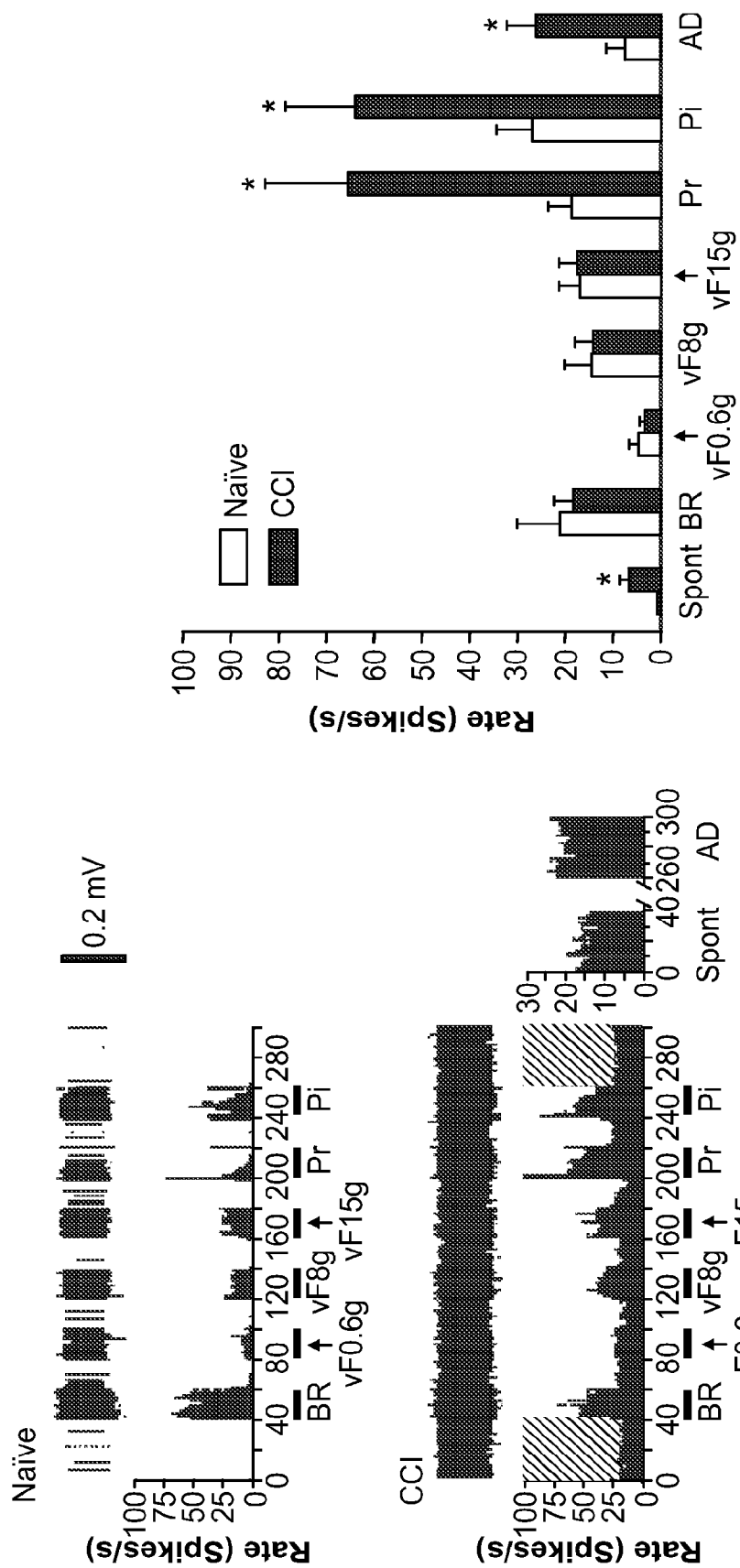
FIG. 18A is a line graph.
FIG. 18B is a bar graph.
Figure 25:
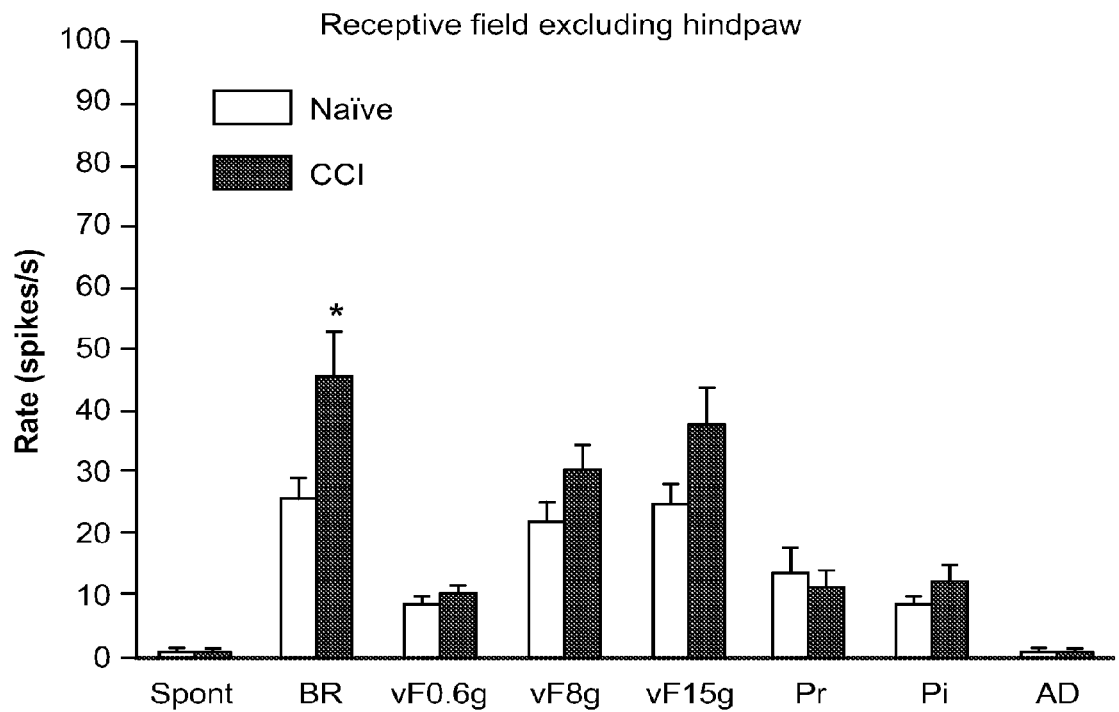
FIG. 25 is a bar graph showing mean rate of firing in VPL neurons with receptive fields excluding the hindpaws from two groups of naïve and CCI rats (n=9-11/gr), showing no difference in firing rates except for firing evoked by brush.
Figures 29, 29A:
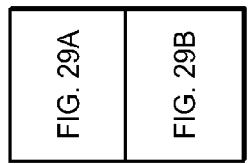

Extracellularly recorded action potentials were isolated from single units in the VPL nucleus of the thalamus under deep anesthesia using template matching techniques. All units discharged action potentials at relatively constant voltage amplitudes and responded with increased firing rates to contralateral mechanical stimuli. In a representative example from a naïve rat, peristimulus time histogram shows increased firing rate when noxious and non-noxious stimuli are applied to the receptive field in the contralateral hindpaw, noting a graded response to increased strengths of von Frey filaments, compared to almost absent spontaneous firing (FIG. 18A, upper panel). Seven days after CCI, evoked responses to pressure and pinch stimuli are increased, while spontaneous activity and afterdischarge are elevated (FIG. 18A, lower panel). Compared to naïve rats, the mean firing rates of VPL neurons with receptive fields in the contralateral hindpaw in rats with CCI increased significantly in response to brush and pinch to 246% and 137%, respectively, with emergence of ectopic spontaneous activity and significant elevation of afterdischarge to 243% (FIG. 18B and Table 1 (FIG. 29)). In contrast, the mean frequency of evoked responses to brush and von Frey filaments (0.6, 8 and 15 g) in rats with CCI were not significantly different from corresponding values in naïve rats. Thus, sciatic neuropathy is associated with plasticity of WDR neurons in the VPL with receptive fields in the contralateral injured hindpaw. Plasticity manifests as selective hyperexcitability in response to non-noxious pressure and noxious pinch, in addition to an emergence of un-evoked firing at a high rate. Of note, evoked responses to von Frey filaments (0.6, 8 and 15 g), pressure and pinch of VPL neurons with somatic receptive fields excluding the hindpaws in rats with CCI were not significantly different from corresponding values in naïve rats, except for a significant increase in brush-evoked responses after CCI, whereas spontaneous activity and afterdischarge were less than 1 Hz in both naïve and CCI rats (FIG. 25).

Figure 19A:
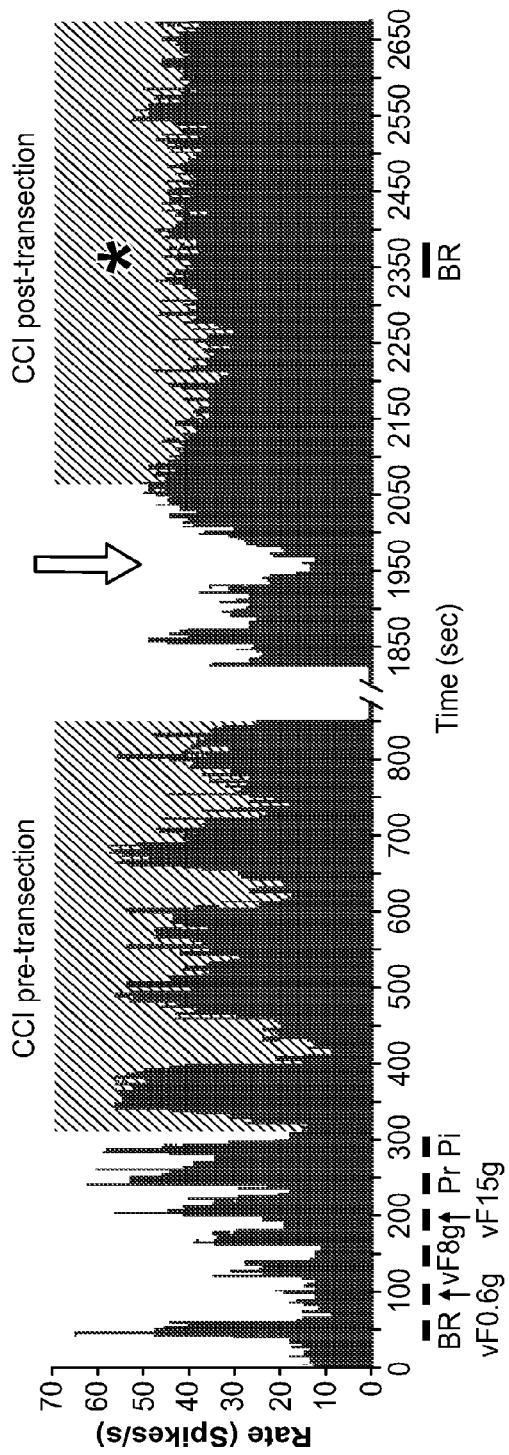
FIGS. 19A-B are line graphs.
Figure 19C:
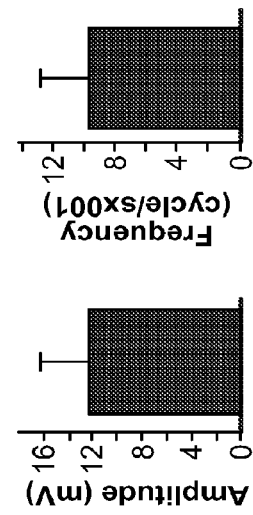
FIG. 19C is a bar graph.
Figure 19B:
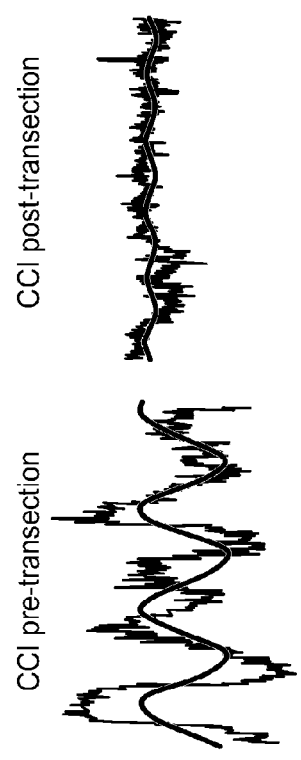

In addition, spontaneous rhythmic oscillation was observed in 33% of VPL neurons recorded from rats with CCI. In one representative example, the firing rate during oscillatory epochs reached that of the pinch-evoked response. However, rhythmic oscillation and brush-evoked responses were abolished by complete transection of the spinal cord at thoracic level, whereas spontaneous firing remained high (FIG. 19A). One example (FIG. 19B) shows a peristimulus rate histogram of the same unit superimposed over a sinusoidal curve during the period of rhythmic oscillation (before transection) compared to nearly flat rate histogram after transection. Mean amplitude and frequency of sinusoidal curves were 24.4±8.2 spikes/s (peak-to-peak) and 0.0095±0.00035 cycle/s, respectively (FIG. 19C). These data indicated that, in addition to the high spontaneous firing rate, sciatic neuropathy is correlated with a rhythmically ectopic firing pattern in a group of VPL neurons dependant on on-going peripheral and/or ascending input below thoracic level.

Figure 26A:
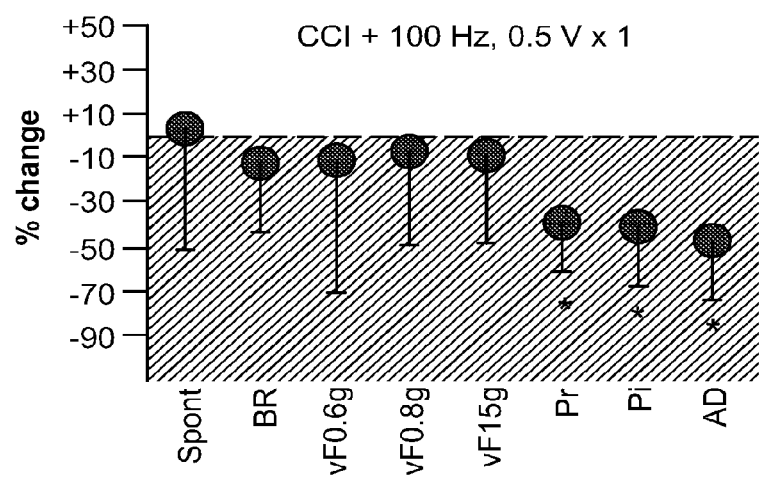
FIG. 26A-B are graphical representations showing mean percent change in firing rates in two groups of VPL neurons under CCI and naïve conditions.
Figure 26B:
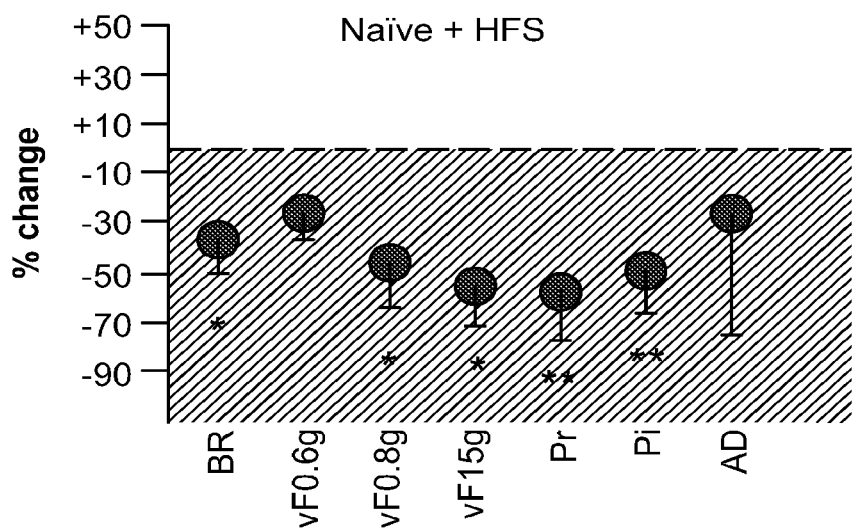

To test whether microstimulation within the VPL modulates the firing of single units, HFS was delivered through the recording electrode and the rate of firing was measured before and after micro stimulation. In rats with CCI, graded attenuation of evoked firing was achieved with incremental increase in voltage amplitude at 100 Hz and a prominent effect was noted at 1.5 V, whereas spontaneous activity was not affected (FIG. 20A). Results with 100 Hz and 200 Hz were comparable and therefore pooled together collectively. All mean firing rates were significantly decreased up to approximately −50% within 10-15 min after HFS for all firing modes except spontaneous activity (FIG. 20C and Table 2). By comparison, LFS at 25 Hz had no significant effect on neuronal firing in rats with CCI at 1.5V, the same voltage amplitude which was otherwise effective with HFS (FIG. 20B, D and Table 2). Results with 25 Hz and 40 Hz were comparable and therefore pooled together. Interestingly, even 'moderate' HFS (mFHS; 1×100 Hz, 0.5 V, 1 s) resulted in significant percent decreases in the firing rates of pressure and pinch-evoked responses and afterdischarge in rats with CCI. In naïve rats, HFS also attenuated all evoked responses except for von Frey 8 g filament (FIG. 26 and Table 4). Therefore, microstimulation within the VPL at high (>100 Hz), but not low (>40 Hz) frequency effectively reverses neuroplasticity induced by sciatic neuropathy by attenuating evoked firing and afterdischarge.

Figure 21:
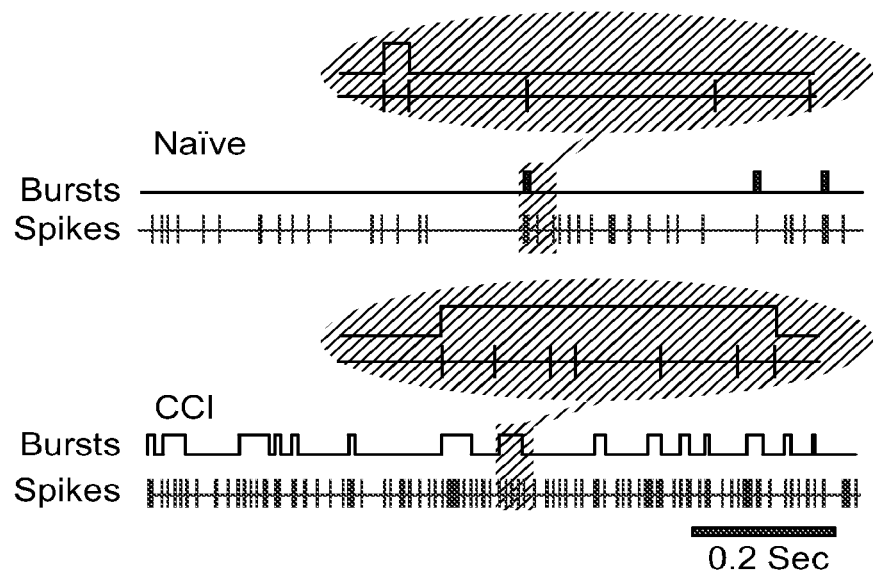
FIG. 21 is a graphical representation showing examples of burst firing under naïve and CCI conditions during peripheral brush stimulation. Upper traces in each panel represent burst activity with corresponding spiking activity in lower traces (shaded insets represent expanded time scales of activity periods in grey boxes). Note increased burst events and number of spikes per burst after CCI.
Figure 22:
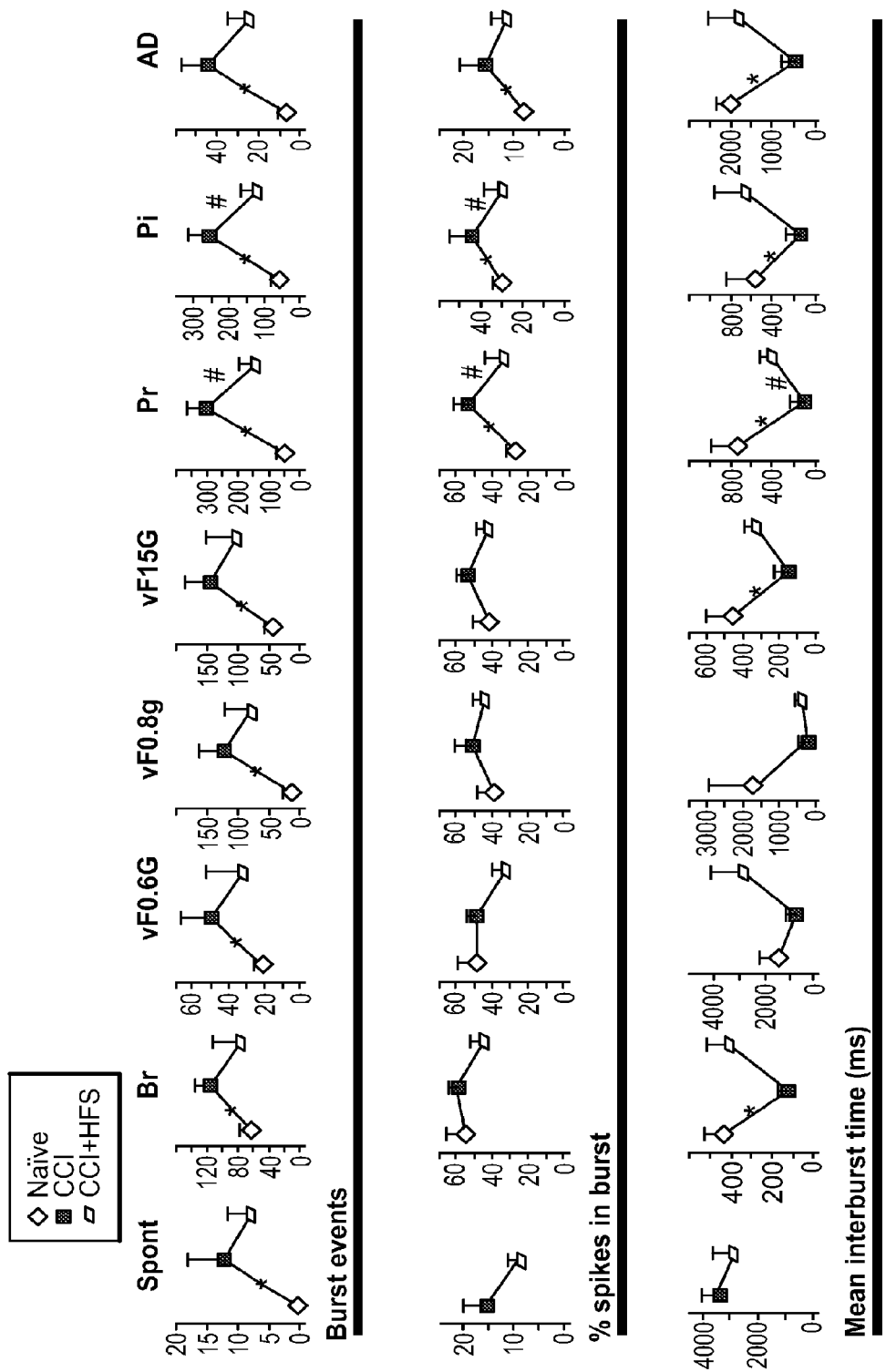
FIG. 22 is a series graphical representations showing a detailed analysis of burst firing showing significantly different patterns in rats with CCI compared to naïve. Evoked burst activity occurred in naïve and CCI rats (although spontaneous burst was very rare in naïve rats). Burst parameters were different in CCI rats, showing a consistent increase in the number of bursts and % spikes for all firing modalities, whereas inter-burst periods were consistently decreased. HFS reversed these changes to near 'normal' or naïve values.

Because tonic and burst firing contribute to signal processing, several burst parameters were measured for single units in the VPL with contralateral hindpaw receptive fields in naïve rats and in those with CCI. FIG. 21 shows examples of burst firing during brush-evoked responses from a naïve rat and another rat seven days after CCI. In naïve rats, spontaneous bursts events were almost absent, whereas those in rats with CCI were increased in number (FIG. 22 and Table 3). Spontaneous bursts were detected in only 2 out of 14 units from naïve rats (mean burst events 0.4±0.3).

Therefore burst parameters during spontaneous activity in naïve rats were not analyzed. In contrast, burst events were increased significantly for all firing modes in rats with CCI compared to those in naïve rats, which were attenuated after HFS with significant changes for pressure and pinch-evoked responses (FIG. 22 and Table 3). Similar trends were observed between groups for percent spikes in burst values, whereas changes in the opposite directions were noted for mean interburst time values (i.e. values decreased for all firing modes in rats with CCI compared to those in naïve rats and were increased after HFS). In general, therefore, bursting patterns consistently deviated from normal after sciatic neuropathy reaching significant levels. These changes were consistently reversed in the normal direction after HFS, indicating that HFS reverses several aberrant features of neuroplasticity including tonic and burst firing properties.

Figure 23:
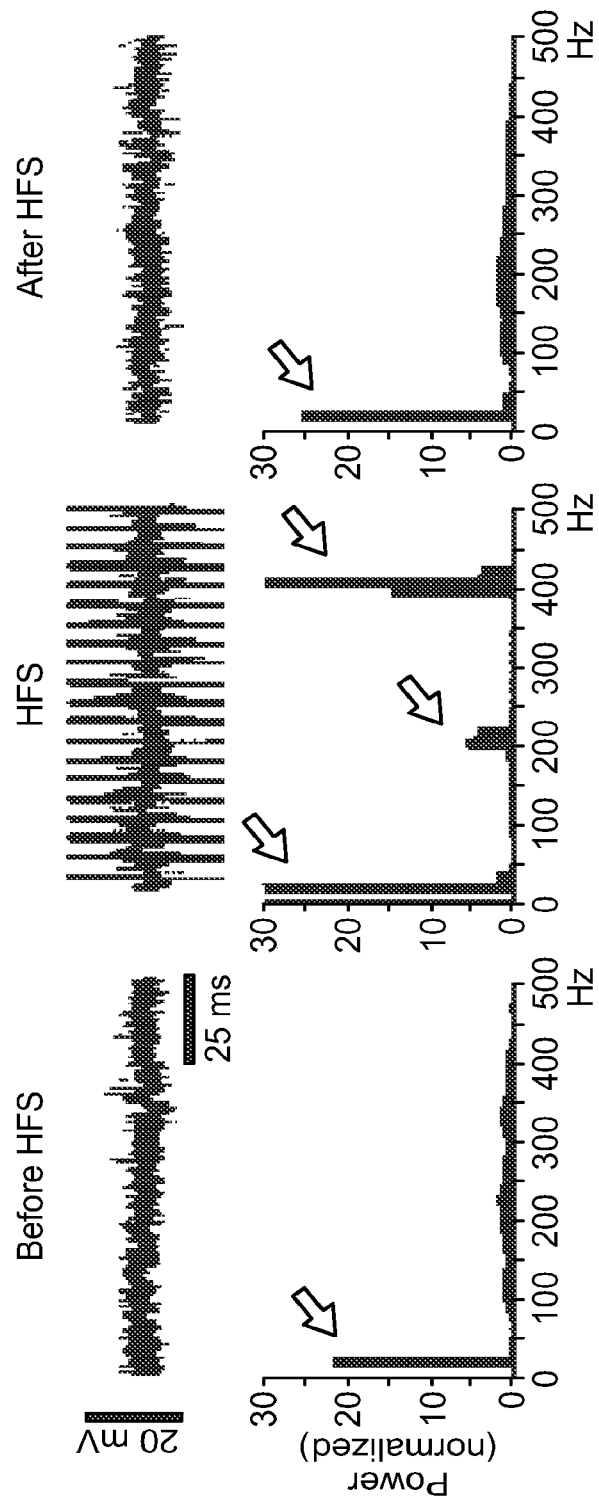
FIG. 23 is a series graphical representations showing local field potentials (upper traces) before, during and after HFS with corresponding power spectra (lower panels) showing a prominent peak between 10-20 Hz (corresponding to β activity; arrow). HFS had no effect on this peak or the overall power distribution up to 500 Hz during spontaneous firing (note emergence of peaks at 200 Hz matching stimulation frequency and a harmonic thereof at 400 Hz; arrowheads).

Although spontaneous tonic and burst firing at the single unit level in rats with CCI was not affected by microstimulation, studies were carried out to determine whether HFS modulates the local field potential within the VPL. Normalized power spectrum (computed by fast Fourrier Transfer and plotted using Spike2) of local field potential recorded from the VPL of a rat with CCI shows a dominant peak in the low $\beta$ frequency range (10-20 Hz) which does not vary significantly in amplitude or frequency before and after HFS (FIG. 23), suggesting HFS causes minimal or no modulation of spontaneous neuronal activity in the VPL at a population level.

Figure 24C:
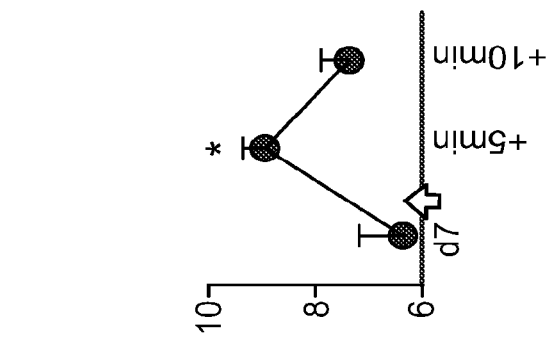
FIGS. 24B-C are line graphs.
Figure 24B:
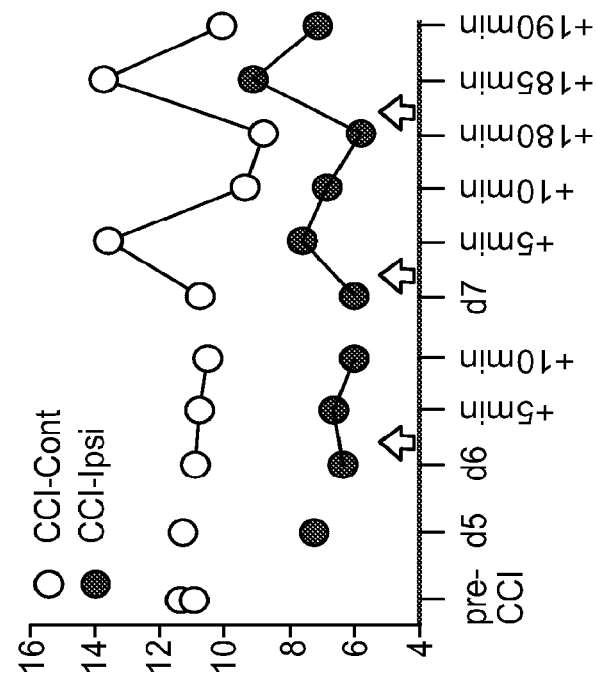
Figure 24A:
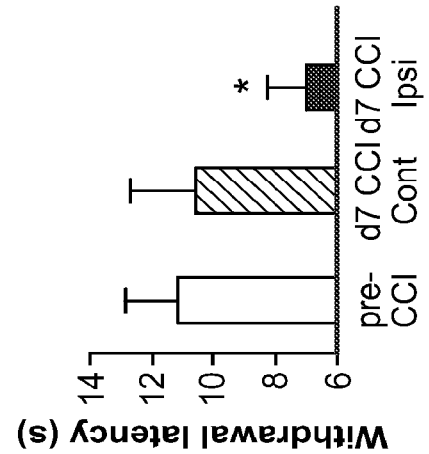
FIG. 24A is a bar graph.
Figure 27:
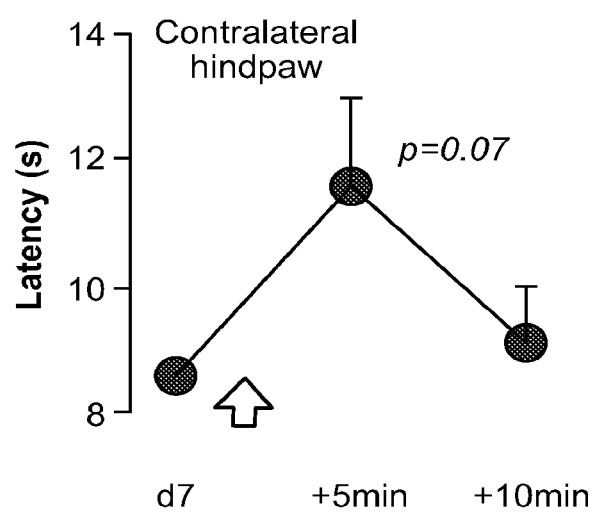
FIG. 27 is a graphical representation showing Mean withdrawal latencies in hindpaws contralateral to injury in CCI rats 5 min before HFS and at 5 and 10 min after HFS showing non-significant change in latency (n=4 rats).

Since HFS parameters comparable to those used in this study have been demonstrated to attenuate CCI-induced allodynia (Kupers R C, Gybels J M (1993) Electrical stimulation of the ventroposterolateral thalamic nucleus (VPL) reduces mechanical allodynia in a rat model of neuropathic pain. Neurosci Lett 150:95-98, hereby incorporated by reference), experiments were carried out to determine whether HFS also modulates thermal hyperalgesia in rats with CCI. Consistent with prior observations using this procedure (Saab C Y, Haim B C (2009) Remote neuroimmune signaling: a long-range mechanism of nociceptive network plasticity. Trends Neurosci 32:110-117; Saab C Y, Shamaa F, El Sabban M E, Safieh-Garabedian B, Jabbur S J, Saade N E (2009) Transient increase in cytokines and nerve growth factor in the rat dorsal root ganglia after nerve lesion and peripheral inflammation. J Neuroimmunol 208:94-103; LeBlanc B W, Iwata M, Mallon A P, Rupasinghe C N, Goebel D J, Marshall J, Spaller M R, Saab C Y (2010) A cyclic peptide targeted against PSD-95 blocks central sensitization and attenuates thermal hyperalgesia. Neuroscience 167:490-500; each of which is hereby incorporated by reference), PWL in the injured hindpaw was significantly decreased to 6.8±1.1 s compared to 10.6±1.9 s in the non-injured hindpaw seven days after CCI, and relative to 11.1±1.6 s for the mean latency of both hindpaws preoperatively (FIG. 24A), indicating that sciatic neuropathy reliably resulted in thermal hyperalgesia. Using bipolar stimulating electrodes chronically implanted contralateral to sciatic injury on the day of CCI, HFS voltage at 1.5 V was delivered within the VPL while testing the thermal withdrawal reflex. Under sham conditions (connecting the electrode to the stimulator without voltage stimulation), withdrawal latency in the injured hindpaw remained decreased compared to the non-injured hindpaw (FIG. 24B). However, withdrawal latency in the injured hindpaw was transiently reversed 5 min after HFS with reproducible effects after 2 hr. The mean withdrawal latency was transiently and significantly reversed from 6.3±0.9 s to 9.1±0.1 s and 7.3±0.1 s at 5 min and 10 min after HFS, respectively, in the injured hindpaw. Of note, the withdrawal latency in the non-injured hindpaw also increased after HFS, however, this change was not significant (FIG. 27).

Lastly, GFAP and OX-42 were quantified in tissue sections in or around the tip of the chronically implanted electrodes in the VPL, which revealed no significant changes in expression compared to the contralateral VPL (FIG. 28), indicating limited glial reactivity to electrode implantation and HFS.

Peripheral neuropathic injury is associated with neuroplasticity of VPL neurons with receptive fields in the contralateral injured hindpaw. Abnormal physiologic properties include higher rate of spontaneous firing, increased rates of afterdischarge and evoked firing in response to non-noxious and noxious mechanical stimuli. In addition, significant changes in burst firing and rhythmic oscillations were observed. Otherwise, the firing of neurons with receptive fields elsewhere in the body was not changed, except for increased responses to brush stimuli.

The data confirmed enhanced spontaneous firing and increased activity evoked by brush, pressure and pinch stimuli in rats ten days after CCI. Noting minor modifications to the CCI model used in this study, these observations were extended to include hyper-responsiveness to von Frey stimulation and afterdischarge at an earlier (day 7) time point concomitant with neuropathic behavior, in addition to other abnormal patterns of tonic and burst firing.

Hyper-responsiveness, rhythmic oscillations and bursting in VPL neurons are observed in a rat model of central neuropathic pain following spinal cord contusion. Relative to neuronal firing in normal rats, firing in rats with spinal lesion alternated between simple, burst and spindle epochs, whereas the number of spikes per burst decreased and interburst interval was not changed. Compared to this study, different lesion sites (sciatic versus spinal) likely account for the incompletely matching patterns of aberrant firing in the VPL. However, spontaneous neuronal discharge in rats with peripheral or central neuropathy remained high after complete transection of the spinal cord, suggesting these changes in specific are likely 'intrinsic' to VPL neurons, while rhythmic oscillations described in this study depend on on-going ascending input.

In addition to firing rate, spike timing is a key factor in determining information content in spike trains. Burst spikes and isolated spikes both contribute to the coding of stimulus-related information (Middleton J W, Yu N, Longtin A, Maler L (2011) Routing the flow of sensory signals using plastic responses to bursts and isolated spikes: experiment and theory. J Neurosci 31:2461-2473; hereby incorporated by reference). Therefore, burst firing is an important feature of the neural code and can effectively impact postsynaptic neurons, including upstream from the VPL in the somatosensory cortex. Bursting can be modulated by the temporal frequency content of incoming signals, which in the case of peripheral neuropathy is significantly altered at peripheral and spinal cord levels. The duration of bursts and the relative timing of burst spikes can encode specific stimulus features. Neurons in the lateral geniculate nucleus discharge bursts and isolated spikes in response to visual stimuli, with different stimulus conditions preferentially evoking different bursting patterns. Bursting has also been reported in thalamocortical projection cells, including the auditory and the somatosensory systems. Although the functional significance of bursting in VPL neurons and modulation thereof under chronic pain conditions are unknown, interestingly, short-term plasticity of thalamocortical synapses is thought to accentuate the sensitivity of cortical responses to ascending sensory input.

Burst firing has been documented in the ventral thalamus in a patient with root injury and occurred during episodes of self-reported touch-evoked allodynia. Direct microstimulation within a thalamic nucleus that contains abnormally active neurons produces burning dysesthesia in patients with spinal deafferentation pain, as well as with root injury pain, whereas microstimulation in the same area might also produce pain relief. These observations suggest that the aberrant physiology of thalamic cells may be directly related to the dysesthesias, whereas the functional outcome depends on the pain condition and the neuro stimulation protocol. It's worth noting that changes in the patterns of burst firing, rather than burst firing pre se, might be a reliable marker for pain-related plasticity. For example, burst firing can occur in deafferented subjects without pain.

HFS in CCI rats caused a 'reversal' effect on abnormal bursting patterns in the direction of normal condition, showing consistent results across all firing modalities. This is in agreement with the premise that HFS in the therapeutic range for motor disorders works mainly by inhibiting neuronal firing or neuronal 'jamming'. The data described herein relates to hyperactive neurons in the VPL and a comparison of the effects of HFS and LFS on neuronal firing at the single unit level. Whereas HFS effectively reversed neuronal hyper-responsiveness, spontaneous activity did not change and overall responsiveness to mechanical stimuli was diminished but not abolished. Prior to the invention, no study compared the effects of varying stimulation frequency on analgesia. It is interesting to note that low frequency (50 Hz) stimulation in the VPL produces little or no analgesia in naïve rats. Data using in vivo and computational models suggest that high frequency signals suppress bursting by transiently interrupting the depolarizations caused by low-frequency signals, for example those evoked by peripheral mechanical stimuli. In a clinical setting, single units in the intralaminar thalamic nuclei of patients with chronic deafferentation pain discharge action potentials spontaneously at a high rate, often rhythmically. In these patients, bursts are described as short (2-6 spikes/burst) with a frequency of 1-4 burst/s, or long (30-80 spikes/burst) with a similar frequency. As described herein, spontaneous burst firing matched well predominantly with the short bursting mode (2.4±0.1 spikes/s and 0.6±0.4 burst/s; values derived from data in FIG. 22 and Table 4).

In rats with central pain, the firing of neurons in the somatosensory cortex is also changed in ways similar to those described for VPL neurons. Dysfunctional thalamocortical communication may underlie cognitive disorders and sensory disturbances resembling tactile allodynia and thermal hyperalgesia, common symptoms of chronic pain. Analysis of magnetic encephalography activity in patients with complex regional pain syndrome shows a distinct shift in power spectra relative to normal subjects, suggesting that the physiological changes in the brain associated with chronic pain may manifest as significant disturbances in network connectivity. Corroborating these electrophysiological data, imaging studies reported several brain regions with decreased grey matter, most commonly in the cingulate, orbitofrontal, and insular cortices. Some studies also show changes in primary and secondary somatosensory cortices and the thalamus. This somewhat diffuse anatomical distribution reflects the co-morbidity of chronic pain with several affective disorders, as well as cofounding variables caused by various medications in clinical studies involving pain patients.

One important consideration is that of potential tissue damage as a result of microstimulation. However, the use of an optimal charge density during microstimulation in behavioral experiments and absence of glial activation indicate little if any tissue damage at the stimulation site using the methods and systems described herein.

The data demonstrated anti-nociceptive effects of HFS on thermal hyperalgesia in rats with CCI, complementing previous data showing similar effects in the mechanical allodynia test in the same animal model, also using HFS of comparable stimulation parameters. It has been demonstrated clinically that electrical stimulation of various sites of the brain, such as the periaqueductal gray matter (PAG), median thalamic nuclei, as well as less commonly targeted areas such as the pontomesencephalic parabrachial region, are effective in relieving chronic pain that is non-responsive to standard pharmacotherapy.

Neurons in the PAG, known to mediate descending anti-nociceptive control unto lumbar dorsal horn neurons, could be activated by electrical stimulation in the VPL, an influence which is not affected by systemic administration of naloxone, suggesting that the VPL-PAG analgesic pathway is unlikely to involve the opioid system. This mechanism provides an alternative explanation to the widely held idea that the analgesic effects of subcortical brain stimulation is the result of activation of a descending 'pain suppressive system' concentrated in the periventricular and periaqueductal regions, which blocks nociceptive transmission at the level of the spinal cord. Primate spinothalamic tract (STT) neurons in the spinal cord are inhibited bilaterally by low current (<25 µA) high frequency (333 Hz) stimulation in the VPL unilaterally, in support of data described herein showing increased withdrawal thresholds in both hindpaws in response to unilateral microstimulation in the VPL. In addition, VPL stimulation may cause sufficient input to the somatosensory cortex to activate corticofugal inhibitory pathways, following thalamocortical-corticofugal projections inhibiting spinal cord nociceptive neurons. It is also possible that VPL stimulation activates antidromically axon collaterals of STT neurons projecting to the medial brain stem, including the PAG and nucleus Raphe Magnus, thus resulting in analgesic effects.

Low-voltage stimulation in the VPL at high frequency can locally inhibit VPL neurons and subsequently the transmission of nociceptive signals to cortical areas. The mechanisms include one or a combination of causes such as 'jamming' of a local nociceptive circuitry, activation of inhibitory structures within a wider network, blockade of membrane ion channels such as voltage-gated currents, depolarization blockade, synaptic exhaustion, and induction of early genes.

Example 2

Objective Diagnostic Index for Pain

Neuropathic pain is a neurological disorder that, prior to the invention, lacked a reliable diagnostic. The methods and systems of the invention provide a solution to a long-standing problem in pain management. An objective measure for pain leads to more accurate diagnosis, monitoring and optimizing therapeutics, thus ameliorating overall clinical outcome. In addition, a physiological correlate of pain is useful in the design of closed-loop neuromodulation systems.

Local field potential (LFP) and multiunit activity are extracellularly recorded signals from a local network of neurons. LFP represents the low-frequency (<0.5 kHz) content of the raw recording generated by membrane currents of the neurons in a local neighborhood of the recording electrode, whereas the high frequency (>1 kHz) content represents neuronal action potential spiking. As such, the coordinated activity of cell populations is reflected by regular oscillations in LFPs, which has been proposed as a mechanism to optimize the recording and analysis of network functions.

LFP is a good candidate for 'pain signature'. Initially studied in great detail owing to their ease of recording with non-invasive macroelectrodes, field potentials contain informative signals measured out of the pool of a large number of spiking neurons while relating to sensory and motor phenomena. Changes in field potentials are triggered by external events (evoked potentials) when induced by a stimulus (e.g. noxious mechanical stimulus or non-noxious tactile stimulus) or by internal cortical dynamics (intrinsic oscillations or rhythms) due to thought processes (e.g. spontaneous pain). Therefore, analysis of LFPs allows for the study of multiple neuronal networks simultaneously, for example thalamo-cortical networks thought to underlie normal states of consciousness and arousal, as well as neurological disorders such as pain and depression. Field potentials are recorded intracortically (LFP, using penetrating electrodes), supracortically (EcoG electrodes), on the scalp (EEG), or even with magnetoencephalograhy (MEG) which measures tangential fields.

The amount of information contained within a brain signal diminishes as it passes from intra- to extra-cellular, from single to multiunit to field potentials, and from LFP to ECoG to EEG to MEG. Many have recently argued in favor of balancing optimal information content with less invasive recording for translational purposes.

Figure 30:
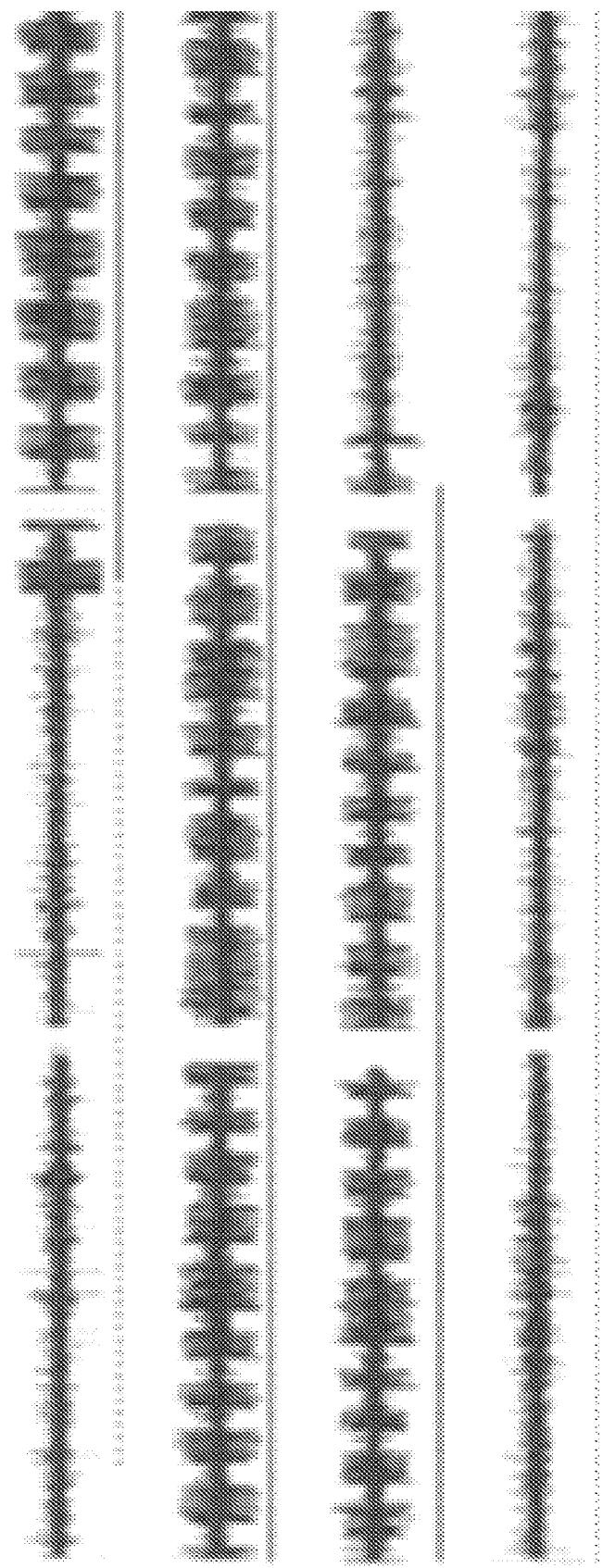
FIG. 30 is a graph showing a representative record of firing of neurons in the thalamus in an awake patient with chronic pain. Pain was repeatedly induced during continuous recording of the neural activity (from upper left to lower right). Dotted lines indicate tapping of the hand for activation of touch-evoked pain. Solid lines indicate pain was verbally reported by the patient.
Figure 31:
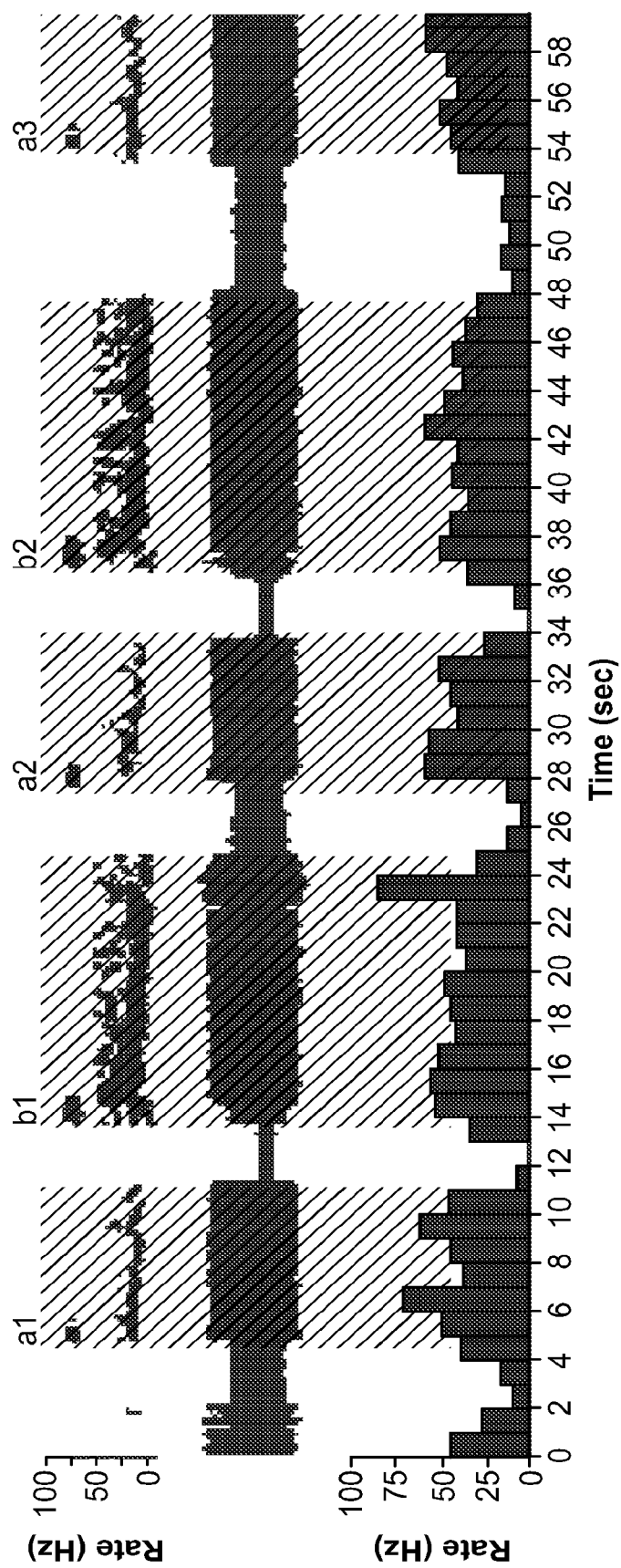
FIG. 31 is a graph of a representative record of a unit in the thalamus of a rat with spinal cord injury pain to illustrate burst events (compare with FIG. 30). During 60 sec of firing activity, 2 burst epochs alternated with unique periods identified as 'a' and 'b'. These 2 epochs spontaneously alternated in a repeated manner separated by interepoch intervals of low firing activity, exhibiting a rhythmic oscillatory firing pattern.
Figure 32:
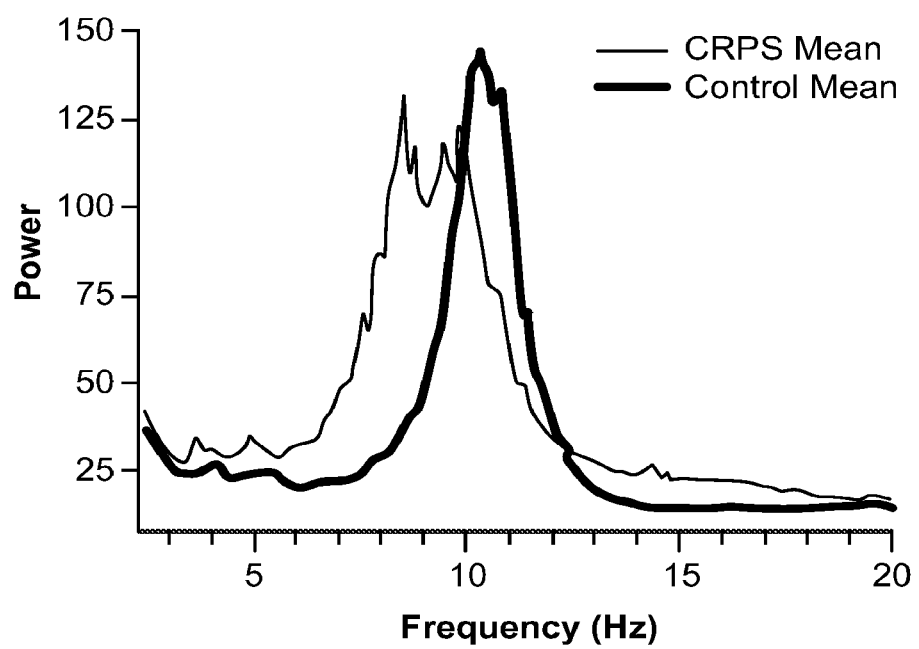
FIG. 32 is a line graph showing a spectral analysis of spontaneous activity. Mean power spectra for patients with Complex Regional Pain Syndrome (CRPS) (red) and normal subjects (black) showing shifting of brain activity to a lower frequency in pain patients.

Data showing pain-related brain activity is described below (FIGS. 30, 31, 32. Characteristic burst firing is recorded from the thalamus of patients with neuropathic pain (FIG. 30). This bursting pattern closely resembles that recorded from the thalamus of an animal model of neuropathic deafferentation pain (FIG. 31), whereby reversal of this neuronal activity was associated with attenuation of pain behavior.

Additional patterns of brain activity in the VPL nucleus of the thalamus related to pain were identified in a rat model of sciatic neuropathy. Recording single-unit action potentials, increased evoked firing were demonstrated in response to tactile noxious and non-noxious stimuli, increased afterdischarge following noxious stimulation, emergence of spontaneous firing, as well as characteristic burst events. Furthermore, deep brain stimulation effectively reversed 'pain signature' and attenuated pain behavior.

A series of psychiatric disorders, including Tourette and pain, may be associated with thalamocortical dysrhythmia (TCD). Synchrony of thalamic and cortical networks under normal conditions are thought to underlie consciousness, whereby state-dependant (sensory or cognitive state) rhythms of thalamocortical relay neurons are continuously driven by corticothalamic input resulting in oscillation, thus binding sensory or cognitive events in a unified percept. Some neurological disorders, however, can lead to disregulation of calcium channels in the brain, thus causing abnormal calcium spiking and high frequency burst in thalamic reticular nuclei, paradoxically driving the thalamocortical network into lower frequency oscillation (4-10 Hz) (FIG. 32). The fact that pain-related changes occur at single unit and MEG levels indicates that LFP (which is intermediate in terms of information content) can be translated into less invasive EEG. Whether it can also be translated into MEG depends to some extent on the results of this study.

Neurons at multiple stages of the somatosensory pathway display oscillations at 7-12 Hz, including in somatosensory cortex (S1) and the ventral posterior nucleus of the thalamus. Therefore, pain is associated with a characteristic pattern of brain activity embodied in LFPs, which is useful for objective diagnosis and as well input signal in a closed-loop technology for pain therapy. Pain-related LFP can be reversed by spinal cord stimulation (SCS) or peripheral nerve stimulation (PNS), thus closing the loop of a hypothetical automated system.

Example 3

Local Field Potential (LFP) Measurements

Methods for single unit recording are described above, and additional studies are described below.

Adult male Sprague Dawley rats (200-250 g) were used. Data were collected and analyzed by observers blinded to the animal's treatment whenever possible.

The pain model utilized chronic constriction injury of the sciatic nerve. This is a widely used model of mononeuropathy that yields reliable pain behavior in rats. Rats are deeply anesthetized with isoflurane (1.5-2%) and the sciatic nerve is loosely ligated with 4 chromic gut (4-0) sutures. After CCI, the overlying muscles and skin are closed in layers with 4-0 nylon sutures.

Pain behavioral is tested daily to determine mechanical and thermal sensory thresholds. Pre-operative testing generally begins 2 days prior to CCI and once per day for 10 days after CCI. Mechanical sensory thresholds are determined by the standard Dixon up-down method utilizing a series of von Frey filaments applied to the glaborous surface of the paw. Thermal hyperalgesia is measured by latency of paw withdrawal in response to a radiant heat source. Rats are placed in Plexiglas boxes on an elevated glass plate under which a radiant heat source (4.7 amps) is applied to the plantar surface of the paw and rats are free to escape from applied stimuli. The temperature that the paw can be subjected to can reach a maximum of 57° C. for a transient time of less than 3 sec. Rats that don't display significant pain behavior are excluded from the study.

Electrophysiology evaluations are carried out as follows. After confirming pain behavior, a minimal craniotomy at day 7 after CCI/sham under deep anesthesia (3% isoflurane) exposes the cortical surface vertically above the VPL or somatosensory cortex (SI) identified according to a rat brain atlas. LFP recordings (CED 1401) are made using a tungsten microelectrode (125 µm, 12 MΩ) by low-pass filtering of the extracellular field potential below 300 Hz. Microelectrodes are positioned stereotaxically in areas of the VPL or SI with identifiable receptive fields in the injured dermatome (hindpaw on the side of CCI). Bands mostly in the low frequency ranges (within the ranges of $\theta$, $\alpha$, and $\beta$ rhythms), as well as higher ranges (100-500 Hz), were studied for 'shifting', spindle wave occurrences and epochs will also be identified. Off-line analysis of spectral power was conducted using Spike 2 software (CED 1401). Evoked responses (triggered by tactile noxious and non-noxious stimuli) and spontaneous activity was recorded. LFP was recorded contralateral to CCI, as well as ipsilateral to CCI in the same animals ('internal' control group), in addition to naïve animals (FIG. 35). Since recording from multiple brain structures will subject an animal to multiple electrode penetrations, separate groups were used for LFP recordings in VPL versus SI.

Statistical analysis was performed using SigmaStat software. Analysis of variance (ANOVA) and parametric tests were used for normally distributed data with p<0.05 considered significant. Otherwise, non-parametric tests were used. Paired t-tests will look at the effect of a manipulation (e.g. evoked responses or the effect of SCS) within the same group of animals (before/after).

Adult male Sprague Dawley rats (220 g) were used to induce chronic pain by chronic constriction injury of the sciatic nerve (CCI). Pain behavior was tested on day 7 post-operatively before brain recording and thermal hyperalgesia was confirmed, showing significant decrease of withdrawal latency in the injured paw compared to the contralateral un-injured paw, a reflex triggered by a controlled radiant heat source.

Figure 33:
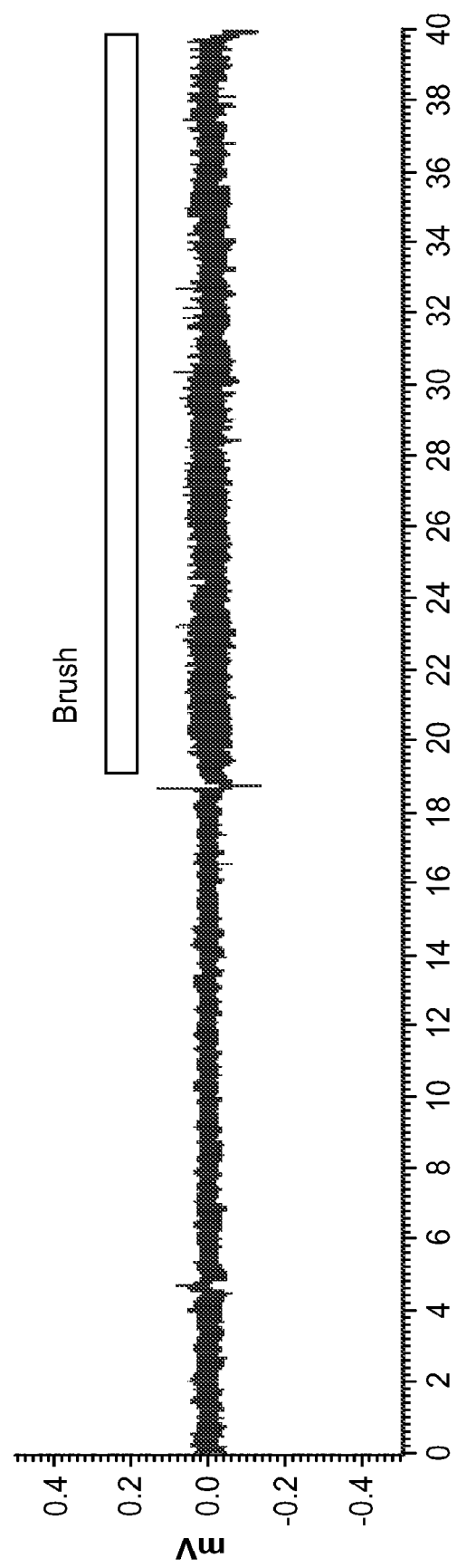
FIG. 33 is a graphical representation of local field potential (LFP) recorded from the VPL contralateral to CCI.

After confirming neuropathic pain behavior, LFP recordings were made under deep barbiturate anesthesia from the ventral posterolateral (VPL) nucleus of the thalamus bilaterally, with the side ipsilateral to injury serving as control (receiving ascending information predominantly from the un-injured paw). The location of the microelectrode was confirmed by stereotaxic coordinates (according to a rat brain Atlas) and by increased in background firing in response to gentle brushing of the corresponding receptive field in the contralateral paw (FIG. 33).

After confirming electrode location in the VPL, spontaneous activity, as well as activity in response to brushing of the contralateral paw, was recorded for 20 s each. Off-line analysis revealed distinct peaks of increased spectral power under different conditions and major differences were found between control (normal side) and CCI (injured side) (FIG. 34).

A reported leftward shift in MEG power spectrum of spontaneous activity in patients with chronic pain compared to control is in agreement with FIG. 34 (left panels). Thalamic LFP recordings from patients with Tourette Syndrome, a cognitive/movement disorder, emphasized a significant correlation between the main LFP frequency and the frequency of single-unit interbursts. Data described herein shows that the mean interburst period of single-unit brush-evoked activity recorded from the VPL is approximately 400 ms for animals with CCI and 100 ms for naïve, thus predicting a rightward shift in power spectra from 2.5 to 10 Hz after CCI, exactly matching with what we show in FIG. 34 (right panels). Therefore, the abnormal bursts described at single-unit level are contributing to the shift in power spectra observed at LFP level. Prominent LFP power spectra was also described in the low frequency (2-7 Hz), as well as in the α-band (8-13 Hz) but virtually absent β activity, also in agreement with FIG. 34 (right panels). A resemblance in brain LFP and EEG activities in the α-rhythms between awake humans and animals under barbiturate anesthesia has been observed, further validating the approach and animal models used in these studies.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Further, while the description above refers to the invention, the description may include more than one invention. While this invention has been particularly shown and described with references to preferred embodiments thereof, it will be understood by those skilled in the art that various changes in form and details may be made therein without departing from the scope of the invention encompassed by the appended claims.

What is claimed is:

1. A system comprising:
   at least one data processor; and
   memory storing instructions which, when executed by the at least one data processor, causes the at least one data processor to perform operations comprising:
      receiving, using the at least one data processor, data characterizing a signal of electrical activity sensed in a patient;
      detecting, using the at least one data processor and the received data, a pain signature relayed via nerves and associated with peripheral damage, wherein the pain signature comprises a pattern of neuronal firing, said pattern comprising an elevated evoked response to stimuli, rhythmic after-discharge signaling, and increased spontaneous background firing, the detecting performed by a pattern recognition component of the at least one data processor;
      determining, using at least one data processor, a treatment protocol in response to the detected pain signature, the treatment protocol including providing at least one electrical signal to the patient comprising one or more electrical pulses being at least about 150 Hz, between about 1 and about 3 volts, between about 1 and about 3 milliampere, and between about 0.25 and about 1 second in duration, the treatment protocol to be delivered to a sensory thalamus contained within the patient via an electrical lead and electrode implantable within the sensory thalamus; and
      causing the treatment protocol to be initiated.

2. The system of claim 1, wherein the peripheral damage is associated with chronic pain.

3. The system of claim 2, wherein the chronic pain comprises one or more of: monoradiculopathies, trigeminal neuralgia, postherpetic neuralgia, phantom limb pain, complex regional pain syndromes, sciatica, and a peripheral neuropathy.

4. The system of claim 1, wherein the peripheral damage comprises inflammation of a nerve.

5. The system of claim 1, wherein the electrical activity is sensed in the patient via non-invasive functional scanning.

6. The system of claim 1, wherein the treatment protocol includes delivering the at least one electrical signal to a wide dynamic range neuron of the patient.

7. The system of claim 6, wherein the wide dynamic range neuron is a physiological correlate of chronic pain.

8. The system of claim 1, wherein the pain signature comprises a pattern of burst-firing, each burst of said burst firing comprising at least 10 times the number of spikes compared to a control non-pain pattern, said burst firing comprising:
   (a) a maximum interval signifying burst onset (6 ms);
   (b) a maximum interspike interval (9 ms);
   (c) longest increase in interspike interval within a burst (2 ms); or
   (d) a minimum number of spikes within a burst (2).

9. A method for implementation by at least one data processor forming part of at least one computing system, the method comprising:

receiving, using the at least one data processor, data characterizing a signal of electrical activity sensed in a patient;

detecting, using the at least one data processor and the received data, a pain signature relayed via nerves and associated with peripheral damage, wherein the pain signature comprises a pattern of neuronal firing, said pattern comprising an elevated evoked response to stimuli, rhythmic after-discharge signaling, and increased spontaneous background firing, the detecting performed by a pattern recognition component of the at least one data processor;

determining, using at least one data processor, a treatment protocol in response to the detected pain signature, the treatment protocol including providing at least one electrical signal to the patient comprising one or more electrical pulses being at least about 150 Hz, between about 1 and about 3 volts, between about 1 and about 3 milliampere, and between about 0.25 and about 1 second in duration, the treatment protocol to be delivered to a sensory thalamus contained within the patient via an electrical lead and electrode implantable within the sensory thalamus; and causing the treatment protocol to be initiated.

10. The method of claim 9, wherein the peripheral damage is associated with chronic pain.

11. The method of claim 10, wherein the chronic pain comprises one or more of: monoradiculopathies, trigeminal neuralgia, postherpetic neuralgia, phantom limb pain, complex regional pain syndromes, sciatica, and a peripheral neuropathy.

12. The method of claim 9, wherein the electrical activity is sensed in the patient via non-invasive functional scanning.

13. A non-transitory computer program product storing instructions, which when executed by at least one data processor of at least one computing system, implement a method comprising:

receiving, using the at least one data processor, data characterizing a signal of electrical activity sensed in a patient;

detecting, using the at least one data processor and the received data, a pain signature relayed via nerves and associated with peripheral damage, wherein the pain signature comprises a pattern of neuronal firing, said pattern comprising an elevated evoked response to stimuli, rhythmic after-discharge signaling, and increased spontaneous background firing, the detecting performed by a pattern recognition component of the at least one data processor;

determining, using at least one data processor, a treatment protocol in response to the detected pain signature, the treatment protocol including providing at least one electrical signal to the patient comprising one or more electrical pulses being at least about 150 Hz, between about 1 and about 3 volts, between about 1 and about 3 milliampere, and between about 0.25 and about 1 second in duration, the treatment protocol to be delivered to a sensory thalamus contained within the patient via an electrical lead and electrode implantable within the sensory thalamus; and causing the treatment protocol to be initiated.

14. The computer program product of claim 13, wherein the peripheral damage is associated with chronic pain.

15. The computer program product of claim 14, wherein the chronic pain comprises one or more of: monoradiculopathies, trigeminal neuralgia, postherpetic neuralgia, phantom limb pain, complex regional pain syndromes, sciatica, and a peripheral neuropathy.

16. The computer program product of claim 13, wherein the electrical activity is sensed in the patient via non-invasive functional scanning.

* * * * *